United States Patent
Wallace

(10) Patent No.: US 12,144,548 B2
(45) Date of Patent: *Nov. 19, 2024

(54) SYSTEM AND METHOD ENABLING AFFORDABLE MEASUREMENT, MONITORING AND REPORTING OF INTRA-OCULAR PRESSURE, COMBINED WITH SYSTEM FOR TOPICAL MEDICATION DELIVERY, APPROPRIATE FOR OFFICE OR HOME-BASED USE

(71) Applicant: David A Wallace, Los Angeles, CA (US)

(72) Inventor: David A Wallace, Los Angeles, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 17/885,632

(22) Filed: Aug. 11, 2022

(65) Prior Publication Data

US 2022/0378290 A1 Dec. 1, 2022

Related U.S. Application Data

(63) Continuation of application No. 16/192,784, filed on Nov. 15, 2018, now Pat. No. 11,412,929.

(Continued)

(51) Int. Cl.
*A61B 3/16* (2006.01)
*A61B 3/00* (2006.01)
(Continued)

(52) U.S. Cl.
CPC .............. *A61B 3/16* (2013.01); *A61B 3/0025* (2013.01); *A61B 3/0033* (2013.01);
(Continued)

(58) Field of Classification Search
CPC ... A61B 3/16; A61B 2562/028; A61B 5/6821; A61B 2562/0247; A61B 3/0033;
(Continued)

(56) References Cited

U.S. PATENT DOCUMENTS

| 4,766,904 | A | * | 8/1988 | Kozin | ...................... | A61B 3/16 |
| | | | | | | 600/405 |
| 6,394,968 | B1 | * | 5/2002 | Wallace | ................... | A61B 3/16 |
| | | | | | | 600/398 |

(Continued)

FOREIGN PATENT DOCUMENTS

CN 105982649 A * 10/2016 ............. A61B 3/107

*Primary Examiner* — Adam Marcetich
(74) *Attorney, Agent, or Firm* — Mark R. Kendrick

(57) ABSTRACT

A combined intraocular pressure (IOP) measuring and eye medication dispensing device may include a first micro-electro-mechanical-system (MEMS) sensor to generate IOP measurements of a living organism's eye; a medication dispensing device to dispense medication into the living organism's eye; a second MEMS micro-dispenser to interface with the medication dispensing device and to control the dispensing of the medication into the living organism's eye; and an analog-to-digital (A-to-D) converter to receive control signals. The A-to-D converter may communicate the control signals to the first MEMS sensor or the second MEMS micro-dispenser; receive the generated IOP measurements from the first MEMS sensor; receive medication dispensing parameters from the second MEMS micro-dispenser or medication dispensing device, and communicate the generated IOP measurements or the medication dispensing parameters. The device may also include a communications interface to receive the control signals from one or more processors in an external control module.

20 Claims, 17 Drawing Sheets

Related U.S. Application Data

(60) Provisional application No. 62/588,278, filed on Nov. 17, 2017.

(51) Int. Cl.
| | |
|---|---|
| *A61F 9/00* | (2006.01) |
| *A61M 5/168* | (2006.01) |
| *A61M 5/172* | (2006.01) |
| *G16H 20/17* | (2018.01) |
| *G16H 50/20* | (2018.01) |

(52) U.S. Cl.
CPC .......... *A61F 9/0008* (2013.01); *A61F 9/0017* (2013.01); *A61M 5/16831* (2013.01); *A61M 5/1723* (2013.01); *G16H 20/17* (2018.01); *G16H 50/20* (2018.01); *A61B 2505/07* (2013.01); *A61B 2560/0418* (2013.01); *A61B 2562/028* (2013.01); *A61M 2205/3303* (2013.01)

(58) Field of Classification Search
CPC ... A61B 3/165; A61B 5/0059; A61B 2505/07; A61B 2560/0418; A61B 5/4839; A61B 5/4836; A61B 2090/064; A61F 9/0017; A61F 9/0008; A61F 9/00781; A61F 9/0026; G16H 40/67; G16H 50/20; G16H 15/00; G16H 20/17; G16H 20/13; A61M 5/1723; A61M 2205/3303; A61M 5/16831; A61M 2210/0612

See application file for complete search history.

(56) References Cited

U.S. PATENT DOCUMENTS

| | | | |
|---|---|---|---|
| 11,096,573 B1* | 8/2021 | Wallace | A61B 5/0077 |
| 2002/0173712 A1* | 11/2002 | Feldon | A61B 3/16 600/405 |
| 2004/0204674 A1* | 10/2004 | Anderson | A61F 9/0008 604/66 |
| 2011/0087138 A1* | 4/2011 | Kahook | A61F 9/00781 601/89 |
| 2011/0251585 A1* | 10/2011 | Peyman | A61F 9/0017 604/506 |
| 2012/0062840 A1* | 3/2012 | Ballou, Jr. | G16H 40/63 351/205 |
| 2013/0117696 A1* | 5/2013 | Robertson | G16H 20/10 715/763 |
| 2013/0165762 A1* | 6/2013 | Choo | B82Y 15/00 600/398 |
| 2013/0211395 A1* | 8/2013 | Schwartz | A61F 9/00781 606/28 |
| 2014/0088400 A1* | 3/2014 | Irazoqui | A61B 5/686 600/398 |
| 2014/0160432 A1* | 6/2014 | Brown, Jr. | A61B 3/113 351/208 |
| 2014/0180160 A1* | 6/2014 | Brown | A61B 5/6868 600/544 |
| 2014/0187969 A1* | 7/2014 | Hunter | A61B 3/14 604/521 |
| 2014/0228783 A1* | 8/2014 | Kraft | G07F 15/04 604/300 |
| 2015/0148681 A1* | 5/2015 | Abreu | A61B 5/6821 600/474 |
| 2017/0023486 A1* | 1/2017 | Wang | A61B 3/1208 |
| 2018/0116512 A1* | 5/2018 | Bitoun | A61B 3/165 |
| 2018/0153399 A1* | 6/2018 | Fink | A61B 3/14 |
| 2019/0083306 A1* | 3/2019 | Suen | A61F 9/0008 |
| 2020/0138669 A1* | 5/2020 | Berdahl | A61H 35/02 |

\* cited by examiner

Optical end point at proper applanation

DC waveform of McKay-Marg tonometer

Trans-Scleral System and Method Patent Illustration

Flow diagram of software analysis

Component diagram

SYSTEM AND METHOD ENABLING AFFORDABLE MEASUREMENT, MONITORING AND REPORTING OF INTRA-OCULAR PRESSURE, COMBINED WITH SYSTEM FOR TOPICAL MEDICATION DELIVERY, APPROPRIATE FOR OFFICE OR HOME-BASED USE

RELATED APPLICATIONS

This application is a continuation of and claims priority to U.S. nonprovisional patent application Ser. No. 16/192,784, filed Nov. 15, 2018, entitled "System and Method Enabling Affordable Measurement, Monitoring and Reporting of Intra-Ocular Pressure, Combined with System for Topical Medication Delivery, appropriate for Office or Home-Based Use," which claims priority and is related to U.S. provisional patent application Ser. No. 62/588,278, filed Nov. 17, 2017, entitled "System and Method Enabling Affordable Measurement, Monitoring and Reporting of Intra-Ocular Pressure, Combined with System for Topical Medication Delivery, appropriate for Office or Home-Based Use," the disclosures of which is hereby incorporated by reference in their entirety.

BACKGROUND

Glaucoma is recognized as the second leading cause of adult blindness in the developed world, after cataracts, as is discussed Bulletin of the World Health Organization, Volume 82, Number 11 Nov. 2004. This is a disease state wherein vision damage results from suboptimal regulation of intra-ocular pressure ("IOP"). Elevated hydrostatic fluid pressure within the eye impairs axoplasmic flow in retinal ganglion cell neurons which, in aggregate, comprise the optic nerve. Pressure-related drop-out of nerve fibers in the optic nerve leads to loss of vision, first in the periphery and later encroaching upon central vision.

Measurement of IOP is a key metric in understanding this process. IOP measurement is a component of every routine eye examination as it can identify elevated pressure, a major risk factor for glaucoma. Instruments that measure IOP have historically been used principally by eye care professionals, as most require gentle touching of the central cornea of the eye. The cornea is one of the most sensitive parts of the body, and measurement of IOP typically can only be performed after application of topical anesthetic eye drops. Currently, systems for IOP measurement, called tonometers, are in wide use only in offices of eye care professionals. Sensors of various types are employed to touch the eye surface after instillation of topical anesthetic drops, and the force of flattening, or indentation of the eye surface, is construed to correlate with IOP. Numerous devices now exist for this use, the most common being the Goldmann applanation tonometer and the Tono-Pen tonometer. Devices are described in "Tonometry and Care of Tonometers," Rajat Maheshwari, Nikhil S. Choudhari, and Manev Deep Singh, Journal Current Glaucoma Practice, 2012 September-December; 6(3); 124-130 and "A history of intraocular pressure and its measurement," Stamper RL, Optometry Vision Science, 2011 January; 88(1): E16-28. Both measure IOP by determining the force of flattening of a portion of the central cornea. Virtually all of the available devices for IOP measurement use sensor technology dating from about the 1950s, and measure at the most touch-sensitive part of the eye, the central cornea. These instruments can only be used if topical anesthetic eye drops are instilled before attempting an IOP reading. Topical anesthetic eye drops are not considered safe for patient use, and are therefore generally not available outside an eye care provider's office or emergency room setting.

FIG. 1 illustrates a Goldmann applanation tonometer according to the prior art. For example, the Goldmann applanation tonometer is a purely analog device. FIG. 2 illustrates a Goldmann applanation tonometer attached to a counter-weight system according to the prior art. Introduced in 1950[1], the Goldmann applanation tonometer incorporates a truncated Plexiglas cone connected to a counter-weight system and, attached to a slit-lamp microscope. Making certain assumptions about corneal biomechanics, and assuming that the cornea behaves functionally like a "thin film" for analysis purposes, it uses the Imbert-Fick principle to discern IOP. FIG. 3 illustrates a tension effect of a tear file and its relation to a force of capillary attraction according to the prior art. At a diameter of 3.06 mm, Goldmann determined that the surface tension effect of the tear film was exactly offset by the force of capillary attraction. At this diameter, then, the inward "force of flattening" asserted by the counterweight system exactly equals the force of IOP pushing outward. FIG. 4 illustrates a visually identified endpoint according to the prior art. A visually identified endpoint requiring a trained examiner is necessary to use this device.

FIG. 5 illustrates a McKay Marg tonometer according to the prior art. Another example is the McKay-Marg tonometer, introduced in 1961, which was one of the first electronic devices to use a micromechanical strain gauge transducer to measure IOP. The McKay-Marg device measured DC offset voltage generated by the transducer electronics, which was printed out on scrolling graph paper. FIG. 6 is a graph identifying IOP in proportion to DC voltage offset according to the prior art. As shown in FIG. 6, IOP was determined by identification of an acceptable waveform in the paper, in proportion to DC voltage offset.

FIG. 7 illustrates a Tono-Pen tonometer according to the prior art. The Tono-Pen tonometer incorporates a micromechanical strain gauge transducer very similar to that used by the McKay-Marg device, to measure IOP. The Tono-Pen tonometer incorporated a single-chip microprocessor to digitize the waveform, then uses software algorithms to identify the proper wave patterns, displaying IOP in a digital readout on the Tono-Pen tonometer.

All tonometer instruments in existence to date in the prior art are intended almost exclusively for use by medical professionals. This creates a requirement that patients with elevated IOP or glaucoma must come to an eye care professional's office to have their IOP checked.

Other instruments have been introduced that endeavor to skirt the need for topical anesthetic drop use, but they are either inaccurate, not generally well-accepted, or are not cost-effective enough to have made much impact on global practice patterns.

FIG. 8 illustrates utilizing a Tono-Pen tonometer to measure an anterior sclera of an eye instead of a cornea according to the prior art. U.S. Pat. No. 6,394,968 to David Wallace, claims a modification to the Tono-Pen tonometer to measure on an anterior sclera of the eye instead of a cornea. Such a modification allowed easier use of a Tono-Pen tonometer. This patent was issued for a system and method for measurement of IOP on the anterior sclera. This area of the eye surface is much less sensitive to touch than anywhere on the cornea, and seems appropriate as a target location at which IOP measurement may be performed, without use of topical anesthetic. When inserting and removing soft contact lenses, for example, people routinely touch the anterior sclera of the eye without engendering discomfort or even mild irritation.

It was estimated that in 2010 the number of patients with the most common form of glaucoma, open angle glaucoma ("OAG") was approximately 60 million worldwide. This number is expected to rise to 80 million by 2020 as discussed "The number of people with glaucoma worldwide in 2010 and 2020, Quigley, H. and Broman, A. T. Br. Journal Ophthalmology, 2006 March; 90(3): 262-267). It is recognized that elevation of IOP (ocular hypertension or "OHTN") is a major risk factor for development of glaucoma. OHTN must also be diagnosed and managed by IOP measurement with tonometry instruments. The population affected with OHTN exceeds by a factor a 3× to 4× the size of the population affected by open angle glaucoma ("OAG") as discussed in "Four-year incidence of open-angle glaucoma and ocular hypertension: The Los Angeles Latino Eye Study, Varma R. et al., Los Angeles Latino Eye Study Group, American Journal Ophthalmology, 2012 August; 154(2): 315-325. Therefore, the size of the global market for a tonometer instrument intended for home-based use is in the range of 200 to 300 million.

FIG. 9 illustrates Micro-Electro-Mechanical System (or Micro-Electro-Mechanical-Sensor) ("MEMS") sensors included in modern smart phone according to the prior art. The explosion of smartphone use in the past 10 years has completely changed the landscape for communication and medical monitoring. Smartphones contain a central processing unit ("CPU"), memory, cellular communication chipset, Wi-Fi chipset, and various specialized sensors. These are micro-electro-mechanical sensors referred to in aggregate as MEMS sensors. The MEMS sensors typically contained in a modern smart phone are shown in FIG. 9. FIG. 10 illustrates the wide variety of MEMS sensors employed in modern consumer and smartphone devices according to the prior art, MEMS sensors can measure pressure, temperature, acceleration, position and numerous other metrics. FIG. 11 illustrates applications and/or uses of MEMS sensors according to the prior art. As shown in FIG. 11, MEMS sensors are also used as microphones, inkjet printer ink dispensers, pressure transducers, and have many other broad applications. As shown in FIG. 11, MEMS technology is already in wide use for pressure transducer production (maroon colored column, second from bottom in FIG. 11). Patent Application 20050182312 to Medtronic appears to show a contact tonometer for sensing intra-ocular pressure (IOP) including a micro-electro-mechanical system (MEMS) device forming a transducer/sensor at or in contact with a contact end of the tonometer where the cornea is contacted, electronics receiving an electrical signal from the transducer, and processing the signal to produce a display indicative of intra-ocular pressure.

SUMMARY OF THE INVENTION

Figure 1:
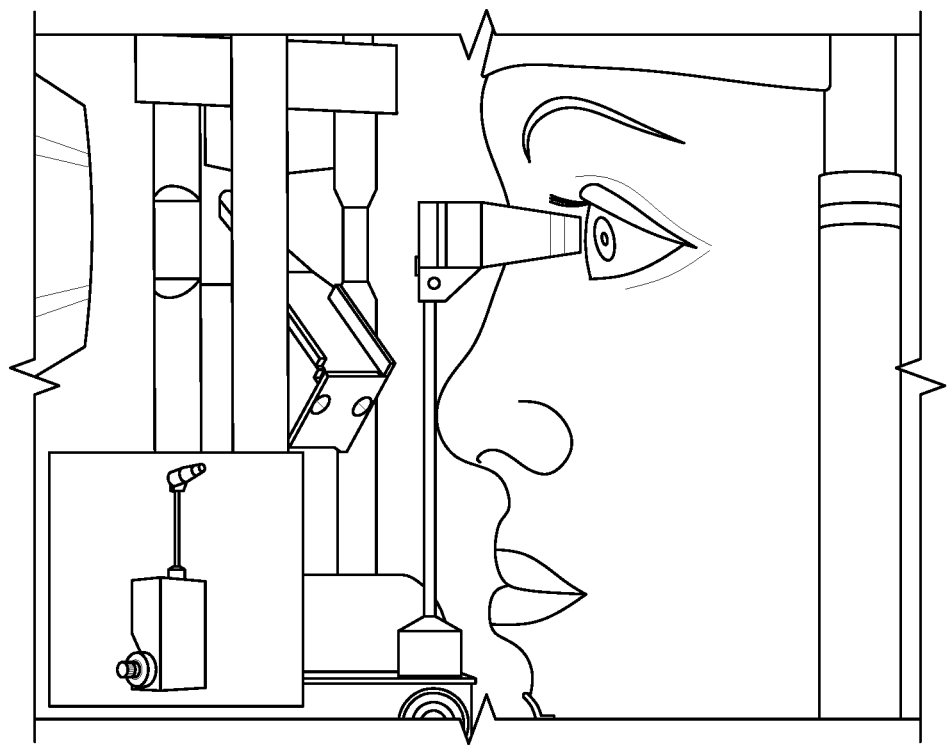
FIG. 1 illustrates a Goldmann applanation tonometer according to the prior art.
Figure 2:
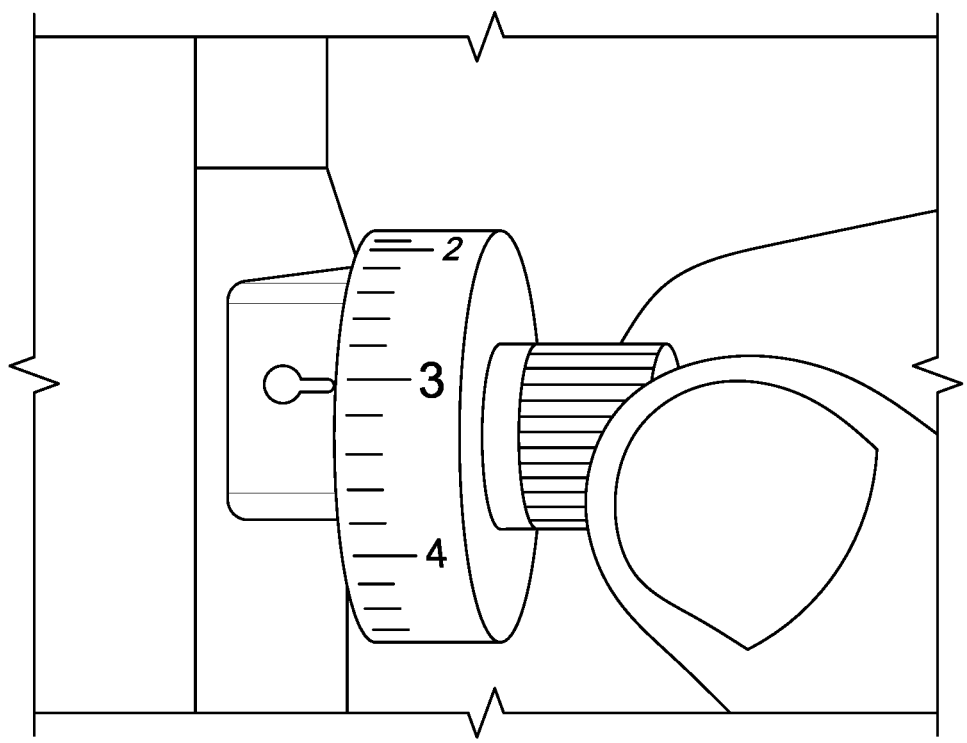
FIG. 2 illustrates a Goldmann applanation tonometer attached to a counter-weight system according to the prior art.
Figure 3:
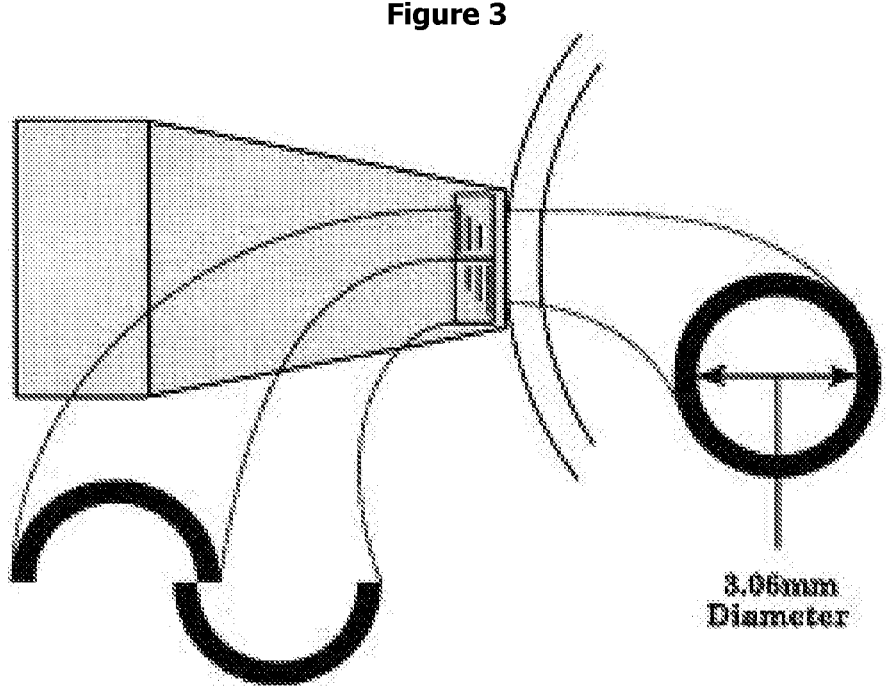
FIG. 3 illustrates a tension effect of a tear file and its relation to a force of capillary attraction according to the prior art.
Figure 4:
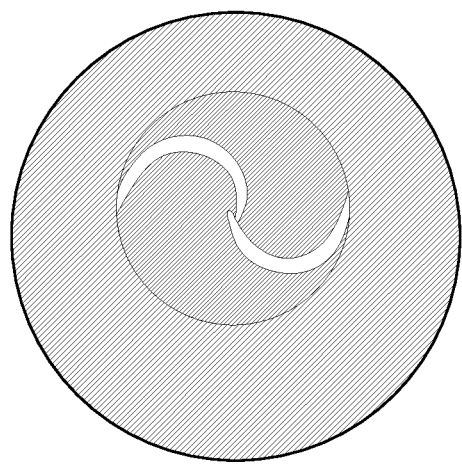
FIG. 4 illustrates a visually identified endpoint according to the prior art.
Figure 5:
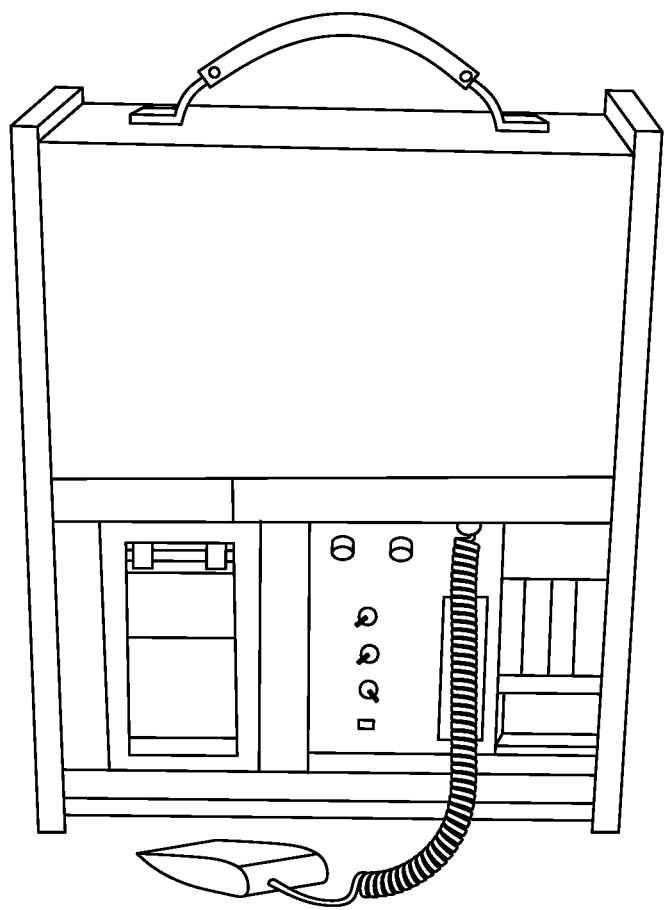
FIG. 5 illustrates a McKay Marg tonometer according to the prior art.
Figure 6:
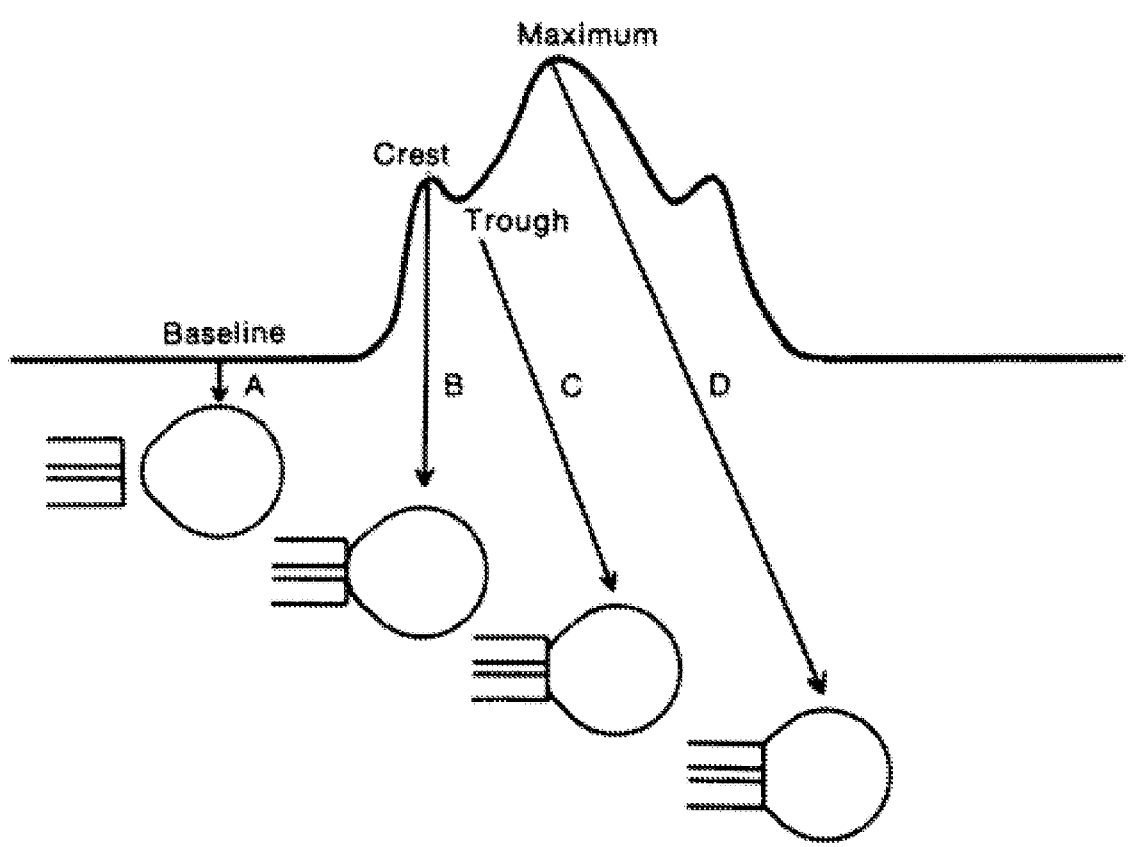
FIG. 6 is a graph identifying IOP in proportion to DC voltage offset according to the prior art.
Figure 7:
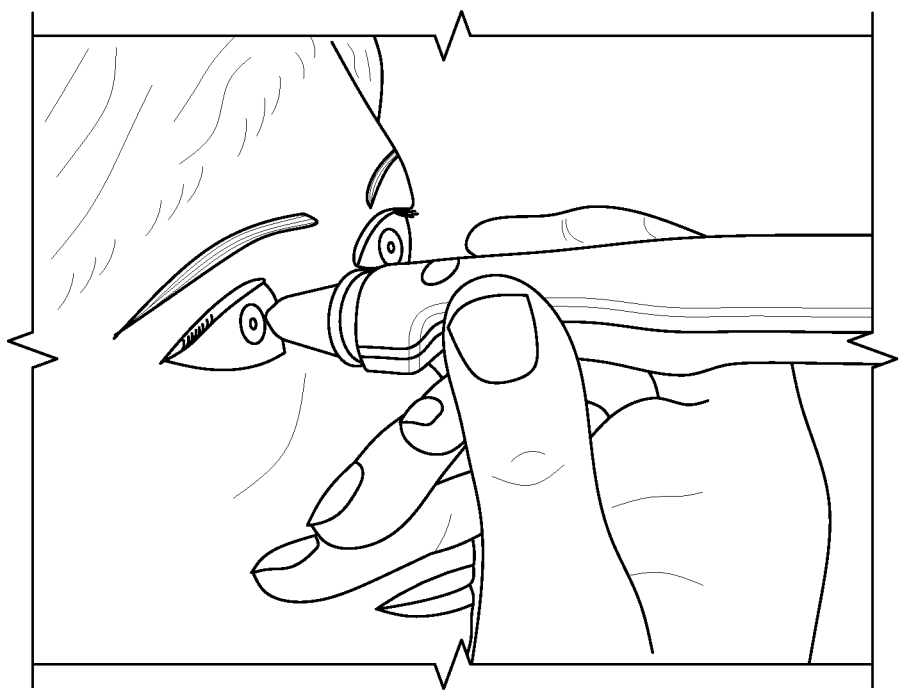
FIG. 7 illustrates a Tono-Pen tonometer according to the prior art.
Figure 8:
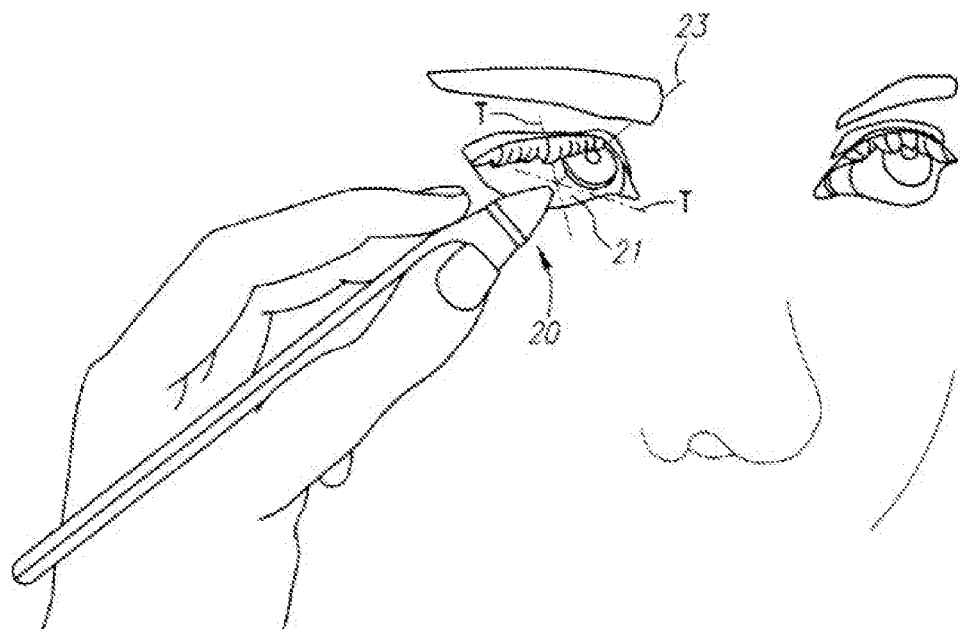
FIG. 8 illustrates utilizing a Tono-Pen tonometer to measure an anterior sclera of an eye instead of a cornea according to the prior art.
Figure 9:
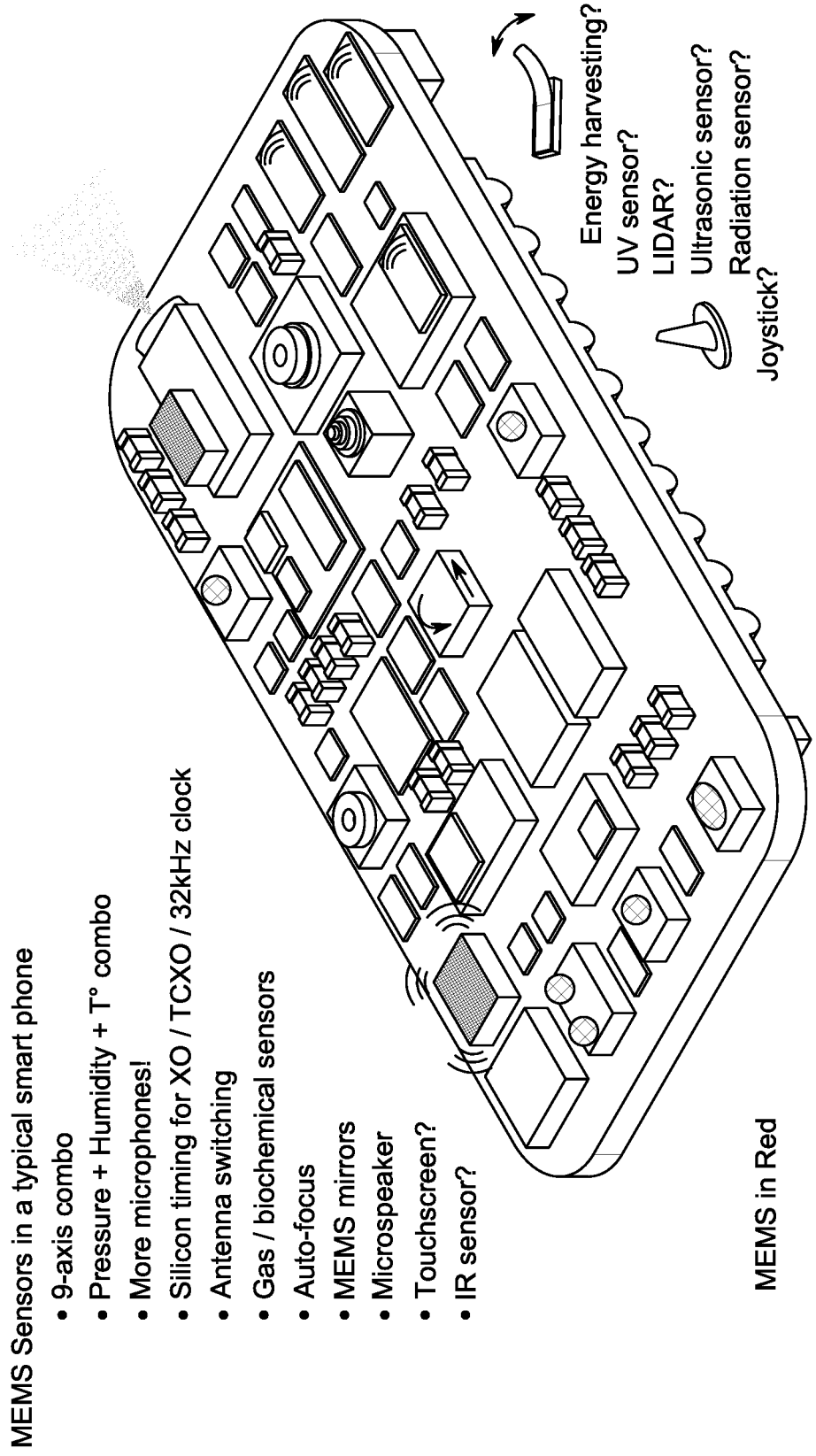
FIG. 9 illustrates MEMS sensors included in modern smart phone according to the prior art.
Figure 10:
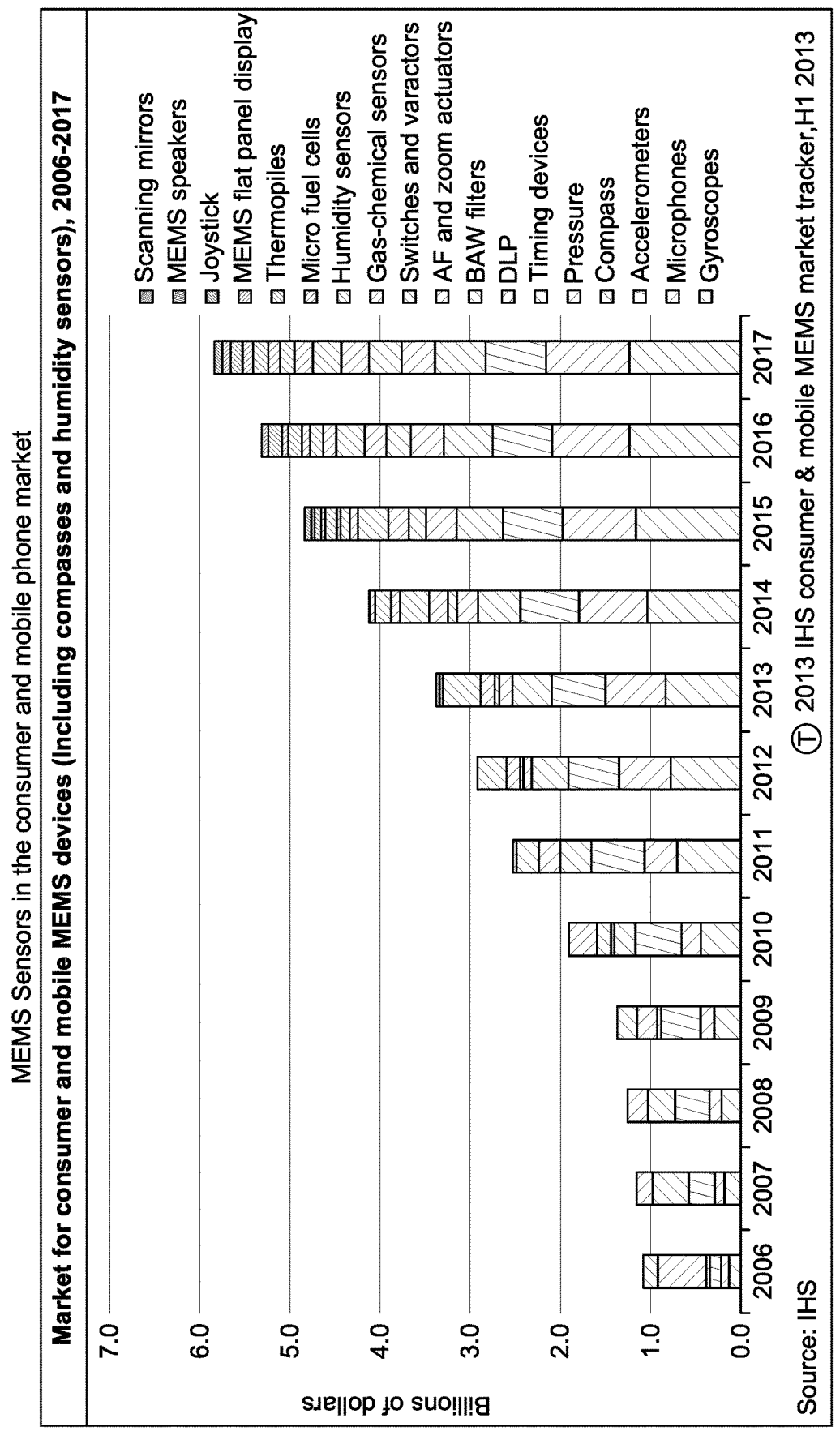
FIG. 10 illustrates the wide variety of MEMS sensors employed in modern consumer and smartphone devices according to the prior art.
Figure 11:
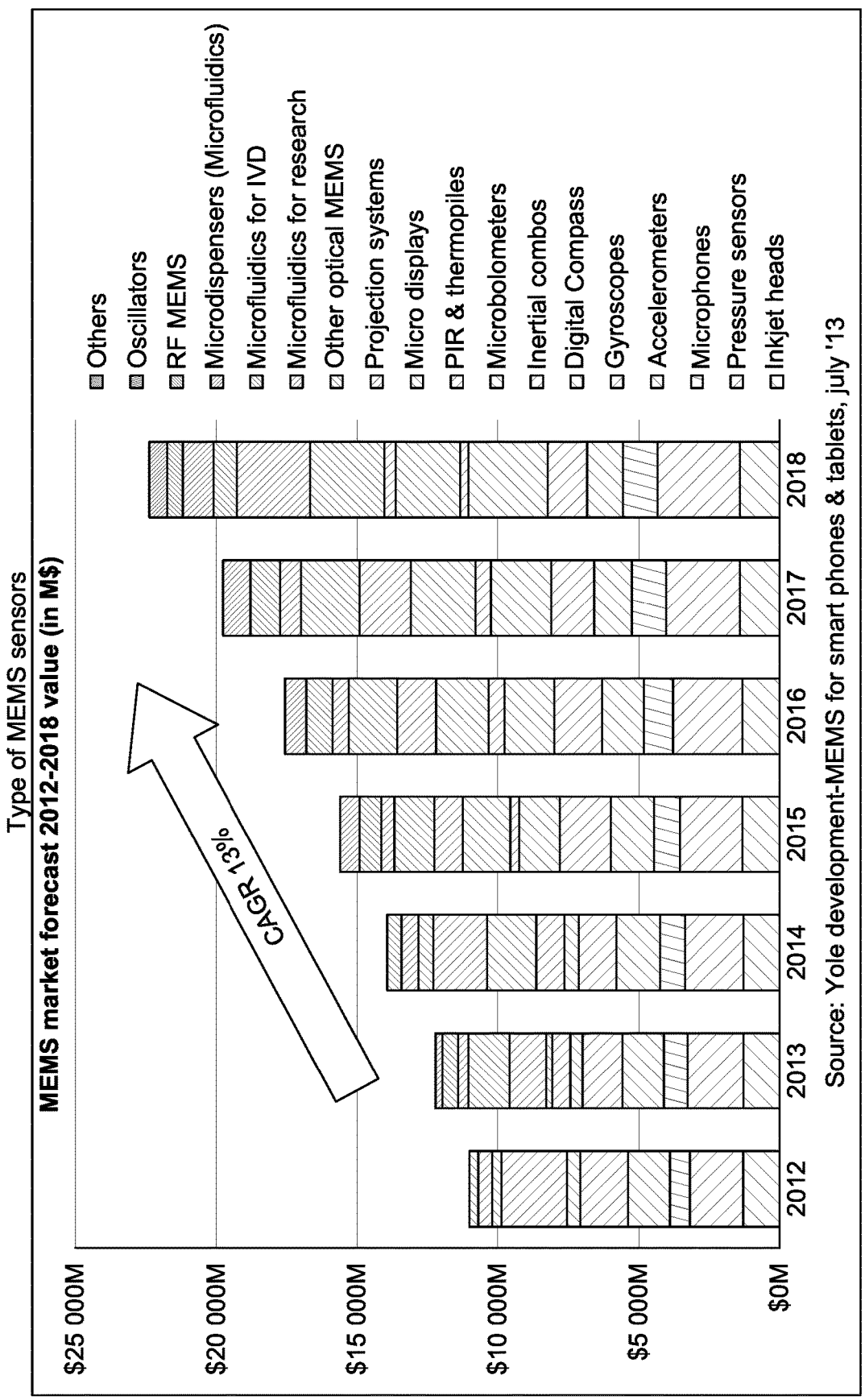
FIG. 11 illustrates applications and/or uses of MEMS sensors according to the prior art.

As discussed previously, current tonometer instruments are not appropriate for use outside the medical practitioner's office setting. Thus, a need exists for instruments that are home-based (e.g., available for use by patients at home) and are able to report measurements and parameters to medical professionals via computing devices.

MEMS technology may be used in micro-fluidics dispensers. However, there has been no discussion of utilizing one or more MEMS sensors in an instrument that can perform IOP measurements and can also concurrently with, or immediately after, dispense medication to lower IOP for a patient. In embodiments, a need exists for such a combined system and method for both measuring IOP and providing drug delivery capability of a very small, calibrated dose of IP-lowering medication in liquid form. Furthermore, this system may provide complete monitoring for eye pressure management purposes and medication effect monitoring, as well as patient compliance monitoring.

A top-level overview of an embodiment is described. In embodiments, a MEMS sensor subsystem at the tip of a hand-held probe may be used to gently touch an eye surface. In embodiments, the probe may be designed to touch the anterior sclera of the eye rather than the central cornea, as this location is much less touch-sensitive. In a fashion analogous to insertion or removal of a soft contact lens, a gentle touch in this area can be employed without use of topical anesthetic eye drops. In embodiments, the MEMS sensor is specifically designed to generate DC voltage proportional to IOP. The DC voltage signal may be digitized by an on-board analog-to-digital converter.

In embodiments, digital signals may be sent or communicated to a base unit or console where a microprocessor may receive the digital signal from the MEMS sensor chip, may read the appropriate waveform information, and may display the IOP measurement numerically on a digital display. In embodiments, the reading may be time-stamped, and may then be stored for later conveyance, or may be immediately conveyed or communicated wirelessly to a smart computing device. In embodiments, a modern smartphone may include chipsets for Wi-Fi, Bluetooth (personal area network), near-field communications (NFC), and/or cellular communications, whereas an iPod Touch may include only Wi-Fi and Bluetooth (personal area network) chipsets. In embodiments, any of these wireless communication chipsets may be sufficient to relay IOP readings or measurements from an IOP monitoring console to a software application, executable by one or more processors, on a connected smart computing device. In embodiments, the IOP readings or measurements may be communicated or transmitted to a networked server computing device and/or database server computing device. In embodiments, the console may be serialized to convey patient- and device-specific identifying information or parameters to any subsequent computing device node in the chain of connected computing devices designed to retain, convey or aggregate such data (e.g., measurements, identifying information and/or parameters). In embodiments, the probe may also be serialized for identification purposes.

In embodiments, a small console to which the digital probe is connected may display (e.g., digitally display) IOP readings or measurements. In embodiments, the probe may be connected to the console by wired or wireless means. When not in use, in embodiments, the probe may rest on the console so that the console secures the probe and positions the probe for charging if the probe is not connected by a wire.

In addition, in embodiments, the probe may comprise another parallel system (or second system) installed therein designed to deliver micro-calibrated amounts of fluid containing IOP-lowering drugs to the patient's eye. In embodiments, this second system may also employ MEMS components acting as micro-dispensers. In embodiments, control circuitry and software stored/resident in the system may be executed by one or more processors to identify when the probe is intending to be used (e.g., being removed from the console holding bracket) and when the probe IOP sensor touches the intended contact surface of the eye. In embodiments, when these conditions are met, the second system may then dispense a calibrated amount of drug to the target tissue if within certain predetermined operating conditions and time windows. This second system may include a MEMS micro-dispenser which may also be referred to as a MEMS sensor.

In embodiments, the dual-function probe including both MEMS subsystems is anticipated to be very cost-effective to produce in large quantities. Therefore, it is feasible to envision that the dual-function probe may be integrated with medication-containing reservoirs containing IOP-lowering medications, and supplied through traditional pharmaceutical channels along with medications intended for topical use. This implies that the MEMS micro-dispensers or reservoirs attached thereto may be replaced on approximately a monthly basis as the medications are refilled. Thus, the combined device may be have a detachable and/or replaceable MEMS dispensing sensor or micro-dispenser assembly which includes a medication-containing reservoirs. Planned replacement in this fashion also protects against incremental contamination, sensor degradation and other potential risks that occur with use of the MEMS sensors or MEMS micro-dispensers. In embodiments, the nozzles may also be replaceable with the micro-dispensers and/or reservoirs. The MEMS sensor for IOP measurement may also be detachable and/or replaceable.

In embodiments, IOP measurements, medication delivery parameters, measurements and parameters relating to a patient, a device, and/or timestamps when IOP readings were generated and when medication is dispensed, along with device identifiers, may be uploaded or communicated to a patient's mobile computing device (e.g. smartphone) software app and/or to central servers and/or central computing devices. In embodiments, from central servers and/or central computing devices, aggregated measurements, parameters and information may be forwarded to eye care provider's computing devices where the aggregated measurements, parameters and information may be sorted by patient, and/or aggregated for research purposes, (or other 'big data' data mining and analysis purposes).

Perceived benefits and/or advantages of this combined IOP measurement and medication dispensing device and/or console may include the following: (1) Enabling real-time reporting of IOP measurements to provider computing devices; (2) Communicating IOP measurements to a patient via a patient's computing device without having to visit a provider office; (3) Facilitating generation and capturing of multiple IOP measurements in a relatively short time frame (formerly referred to as "phasing") to identify if there are particular times of day when a patient's IOP is higher, placing the eye at greater risk of nerve compromise, and guiding therapy accordingly; (4) Encouraging patient compliance with prescribed medication regimen for maintaining IOP control, as prescribed by the eye care provider; (5) Monitoring compliance directly and electronically, with reports to provider computing devices identifying compliance or lapses in same; and (6) Increasing likelihood of accurate drug delivery by a combined IOP measurement and medication dispensing system to a target tissue, since much smaller volumes of more concentrated medication-containing solution may be delivered directly to the eye surface. The combined IOP measurement and medication dispensing system may also (7) reduce likelihood of medication loss by spillage away from the eye, a common problem with standard volumes in existing eye drop delivery systems (bottles); and/or (8) Monitoring IOP measurement and medication dispensing for treatment of glaucoma and ocular hypertension in remote or under-served locations.

DETAILED DESCRIPTION OF THE INVENTION

It would seem desirable to develop an instrument that may measure on a part of the eye less sensitive than the central cornea, and that might be applicable to use both by eye care professionals, medical professionals outside the specialty of ophthalmology, and by patients, in a home-use context. In embodiments, a part of an eye less sensitive than a central cornea may be a sclera.

In the era of "the Internet of Things" (or "IoT") where electronic devices in many different physical locations may be interconnected, a tonometer device (or eye probe or eye examination device) may be designed for home-based use. In embodiments, a tonometer device may connect through Wi-Fi or through Bluetooth (or other wireless communication protocols such as cellular wireless communication protocols, local area network wireless communication protocols, near field communication ("NFC") protocols or personal area network wireless communication protocols) to a smartphone (or other mobile communication device or mobile computing device). In embodiments, the mobile communication or computing device may communicate (via a cellular communications channel, another wireless communications channel, and/or a wired communication channel such as a local area network) to a central server (e.g., or central computing device or database) relaying IOP readings and/or associated measurements to the central server computing device or database). In embodiments, associated measurements may be time stamped information, patient-identifying information and/or device-identifying information. Information may be aggregated at the server level, and distributed to relevant eye care professionals via email or other electronic communication means such as text and/or automatic file uploads. In embodiments, patients might also receive reports pertaining to their IOP readings, and may receive alerts and/or reminders if scheduled IOP measurements are not received.

The above-described instrument and/or device, overall system and methods associated therewith may provide the infrastructure to facilitate: (1) Monitoring of IOP by patients in very remote locations; (2) Compliance monitoring (as to the use of treatment drops, and whether the use is on schedule, according to the recommendations of the eye care professional); and (3) Conveyance of a patient's IOP history and medication history to their primary eye care provider or a referral specialist.

In addition, Internet (or global communications network) uplink of data from the instrument, device, probe and/or console may be accomplished by Bluetooth, near-field communications, Wi-Fi, wireless local area network, and/or wireless personal area network communication with software resident and executable by one or more processors installed in a smartphone. The smartphone may be replaced by a tablet or other low cost or portable computing device, a wireless computing device, a laptop personal computing device, a desktop computing device, a device (or electronic device) including an integrated computer board or single-board computing device.

The instrument, device, probe and/or console described herein may communicate any parameters, timestamps and/or other related information sent over the global communications network (e.g., the Internet). The parameters, timestamps and/or related information communicated over the global communications network (e.g., the Internet) may be compressed, encrypted, de-identified and/or be HIPAA compliant. In embodiments and cases where a wireless communications channel to the smart phone is provided or utilized (Bluetooth, PAN, Wi-Fi, NFC, cellular or USB communication protocols, for example), a serial number of the instrument and/or base unit/console may be placed in the hardware or software and communicated to the smart phone, to prevent unauthorized use of the system. In embodiments, the above-described system and method may also be deployed utilized a "smart" device that communicates with the Internet over Wi-Fi (IEEE 802.11 G) networks rather than cellular (3G) networks. For example, an Apple iPod Touch® contains a hi-resolution camera and processing chipsets comparable to an Apple iPhone®, but does not contain 3 G chipsets for cellular communications.

Figure 12:
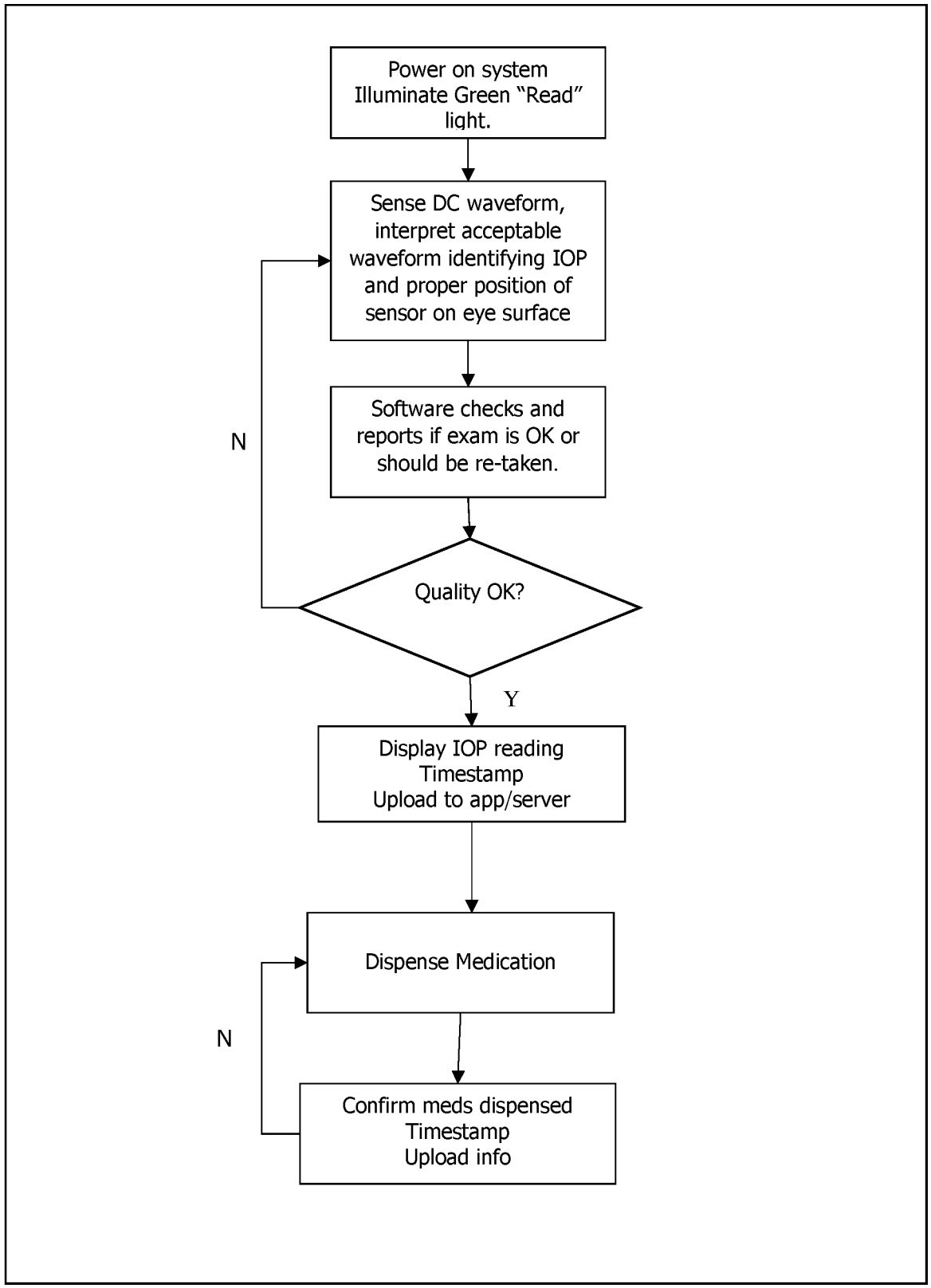
FIG. 12 illustrates a method or process of operating an eye examination wand and/or probe according to embodiments.
Figure 13:
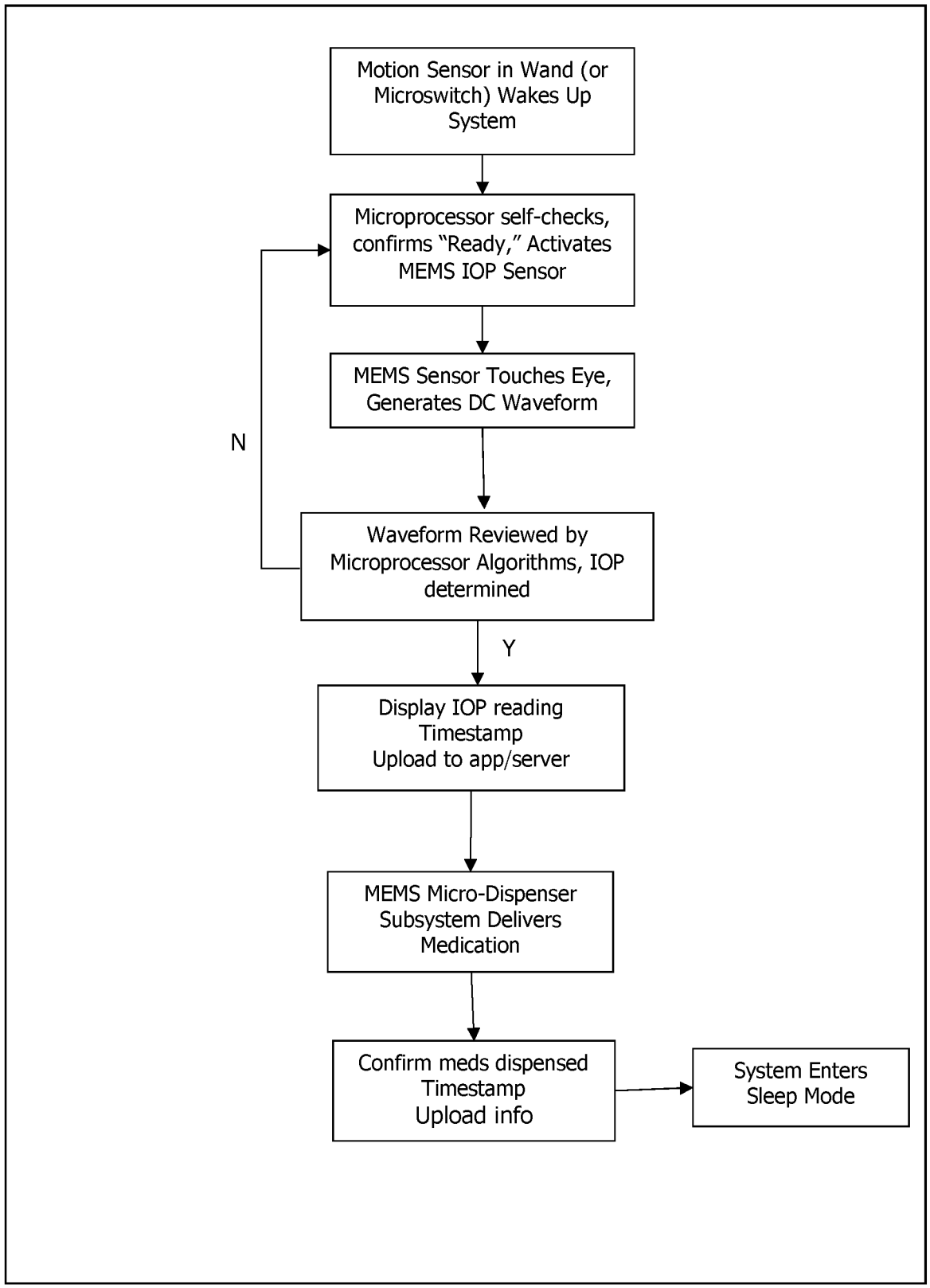
FIG. 13 illustrates a method or process utilizing specific components of eye examination according to embodiments.

FIG. 12 illustrates a method or process of operating an eye examination wand and/or probe according to embodiments. FIG. 13 illustrates a method or process utilizing specific components of eye examination system according to embodiments. Of course, embodiments are intended to be illustrative examples rather than be limiting with respect to claimed subject matter. Likewise, for ease of explanation, an embodiment may be simplified to illustrate aspects and/or features in a manner that is intended to not obscure claimed subject matter through excessive specificity and/or unnecessary details. Embodiments in accordance with claimed subject matter may include all of, less than, or more than blocks 1205-1235 and/or 1305-1335. Also, the order of blocks 1205-1235 and/or 1305-1335 is merely as an example order. In embodiments, an eye examination wand or probe may be referred to as a tonometer. In embodiments, a console or base station may be turned on or activated along with an eye examination probe and, for example, a green light may be illuminated 1205 indicating an eye examination probe may be utilized. In embodiments, an eye examination wand or probe may sense 1210 a DC waveform and interpret the DC waveform identifying IOP and proper positioning on an eye surface. In embodiments, software executable by one or more processors on a base station or console, may check 1215 if an eye examination is OK and acceptable or whether the eye examination may need to be retaken. In embodiments, software executable by one or more processors on a base station or console, may determine 1220 if quality of the IOP measurement of the eye examination is acceptable. If not, the process returns to step 1310 to sense a DC waveform. If the quality is acceptable, a display on a base station or console may display 1225 an IOP measurement, generate a time stamp associated with the IOP measurement, and communicate (e.g., upload) the IOP measurement, associated parameters and/or generated timestamps to a mobile communications device (e.g., smartphone) and/or a cloud-based database server. In embodiments, this may be accomplished utilizing a software application on a mobile communications device. In embodiments, an eye examination wand or probe may dispense medication 1230 in response to instructions and/or signals from a software application on a mobile communication device and/or instructions and/or signals from a console or base unit. In embodiments, a base unit or station or console may verify medication has been dispensed, generate associated medication dispensing parameters, and/or generate one or more timestamps 1235 associated with medication dispensing parameters. In embodiments, this information may be communicated (or uploaded) to the software application on the mobile communications device and/or cloud-based database server. In addition, the IOP measurements, associated parameters, timestamps, and medication dispensing parameters may also have identifiers uploaded and/or communicated to identify which eye examination wand or probe and/or base unit or console uploaded the information.

FIG. 13 illustrates a method or process utilizing specific components of eye examination system according to embodiments. In embodiments, a motion sensor in an eye examination wand or a microswitch in a console or base unit may detect movement and wake up or activate 1305 an eye examination and medication dispensing system (or specific components of an eye examination and medication dispensing system). In embodiments, one or more microprocessors or controllers in a base unit or console may perform a self-check, may confirm the system is ready and may generate commands, instructions and/or signals to activate 1310 an IOP MEMS sensor. In embodiments, an IOP MEMS sensor in an eye examination wand may touch a surface of a patient eye and may generate 1315 a DC waveform. In embodiments, software (e.g., computer-readable instructions) stored in memory of the base unit or console may be executed by one or more processors or controllers and may review received DC waveform and determine 1320 an IOP measurement. In embodiments, a base unit or console may display the IOP measurement, generated associated parameters and generate a timestamp 1325 associated with the IOP measurement. In embodiments, the base unit or console may upload and/or communicate the IOP measurement, associated parameters, and/or timestamp to application software in a mobile communications device and/or a cloud-based database server. In embodiments, software instructions (e.g., computer-readable instructions) may be executed by one or more processor on a base unit or console and may generate commands, instructions and/or signals to activate 1330 a medication dispensing MEMS subsystem to deliver or dispense medication to a patient's eye. In embodiments, software instructions may be executed by one or more processors on a base unit or console and may confirm medication has been delivered and/or dispensed, may generate associated medication dispensing parameters and may generate a timestamp associated with medication dispensing parameters. In embodiments, a base unit or console may upload or communicate 1335 medication dispensing parameters and timestamps to a mobile communication device (and/or software application) and/or to a cloud-based database server. In addition, the IOP measurements, associated parameters, timestamps, and medication dispensing parameters may also have identifiers uploaded and/or communicated to identify which eye examination wand or probe and/or base unit or console uploaded the information. In embodiments, after a specified period of time, one or more components of an eye examination system may enter a sleep mode.

Figure 14:
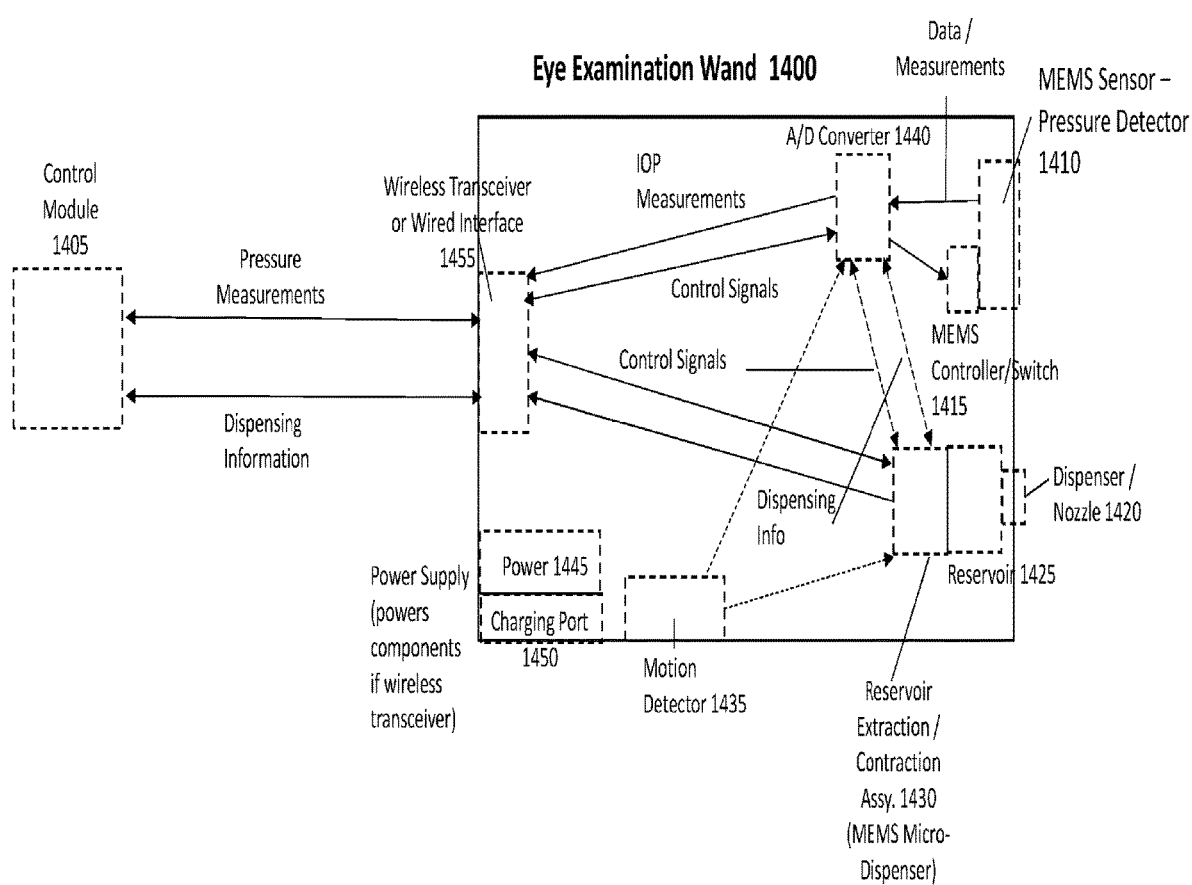
FIG. 14 illustrates an eye examination wand or probe according to embodiments.

FIG. 14 illustrates an eye examination wand or probe according to embodiments. In embodiments, an eye examination wand or probe 1400 may communicate with a base module or control module 1405 via a wired communication interface 1455 or a wireless transceiver 1455. In embodiments, the wireless transceiver may be an integrated circuit which may comprise one or more or Bluetooth wireless transceivers, PAN transceivers, Wi-Fi transceivers, wireless LAN or 802.11 transceivers, Near-field communication (NFC) transceivers and/or cellular communication transceivers (e.g., 3G, 4 G, or 5 G). In embodiments, an eye examination wand or probe 1400 may measure intraocular pressure (IOP) of a patient's eye. In embodiments, an eye examination wand or probe 1400 may be referred to as an IOP measuring device. In embodiments, an eye examination wand or probe 1400 may comprise a micro-electro-mechanical-system (MEMS) sensor 1410, a MEMS switching device or controller 1415, an analog-to-digital (A-to-D) converter 1440, and a communication interface (e.g., a wired communication device and/or a wireless transceiver 1455). In embodiments, a MEMS sensor 1410 may measure, capture and/or generate IOP measurements of a patient's eye. In embodiments, a MEMS pressure sensor 1410 may press against a sclera to capture IOP measurements. In embodiments, a MEMS switching device or controller 1415 may control activation of a MEMS sensor 1410. In embodiments, an A-to-D converter or D-to-A converter 1440 may receive control signals (or instructions) from a base module, console, or control module 1405 and communicate control signals to the MEMS sensor 1410 utilizing the MEMS switching device or controller 1415. In embodiments, the A-to-D converter or D-to-A converter 1440 may receive the generated and/or captured IOP measurements and communicate the generated IOP measurements back to the base module or unit or console 1405. In embodiments, a communications interface 1455 may receive control signals and/or instructions from one or more processors or controllers in a control module or base module 1405 and may communicate control signals to the A-to-D converter or D-to-A converter 1440. In embodiments, a communications interface 1455 may receive generated IOP measurements and/or parameters captured or generated from the MEMS sensor and may communicate the generated IOP measurements to a base unit or control module 1405.

In embodiments, this application may include a micro-dispenser to dispense medication however, this may also be referred to a medication dispensing MEMS sensor 1430. In embodiments, an eye examination wand or probe 1400 may further comprise a medication dispensing MEMS micro-dispenser 1430, a medication reservoir 1425 and/or one or more nozzles or dispensers 1420, an A-to-D converter (or D-to-A converter) 1440, and/or a communications interface 1455. In embodiments, a medication reservoir 1425 may hold and/or contain eye medication. In embodiments, one or more nozzles 1420 may dispense medication into a subject's eye. In embodiments, the subject may be a human, an animal or another living organism having an eye. In embodiments, a medication MEMS micro-dispenser 1430 may interact and/or control a medication reservoir 1425 to control dispensing of eye medication contained in the reservoir 1425 through the one or more nozzles or dispensers 1420 into the patient's eye. In embodiments, an A-to-D converter (or D-to-A converter) 1440 may receive control signals from a control module or base module 1405 (through a communication interface) and may communicate the control signals to the medication MEMS micro-dispenser 1430. In embodiments, the A-to-D converter 1440 may receive medication dispensing parameters from the MEMS sensor or micro-dispenser (e.g., timestamp of dispensing and/or medication levels in reservoir) and may communicate medication dispensing parameters. In embodiments, a communication interface 1455 may receive control signals from one or more processors in a base module, console or control module 1405 and communicate the control signals to an A-to-D converter (or D-to-A converter) 1440. In embodiments, a communication interface 1455 may receive medication dispensing parameters generated by a medication MEMS micro-dispenser 1430 from a A-to-D converter (or D-to-A converter) 1440 and may communicate the generated medication dispensing parameters to the external control module, console or base module 1405.

In embodiments, an eye examination wand or probe 1400 may be a combined IOP measurement and medication dispensing device. In embodiments, such a dual-function device 1400 may comprise a combined intraocular pressure (IOP) measuring and eye medication dispensing device. In embodiments, a combined IOP measuring and eye medication dispensing device 1400 may comprise a first micro-electrical-mechanical-system (MEMS) sensor 1410 to generate IOP measurements at a human or subject eye, a medication dispensing device 1420 1425 to dispense medication into the human or subject eye, and a second MEMS micro-dispenser or sensor 1430 to interface and interact with the medication dispensing device 1420 1425 and/or to control the dispensing of the medication into the human or subject eye. In embodiments, a combined IOP measuring and eye medication dispensing device 1400 may further comprise an analog-to-digital (A-to-D) converter (or D-to-A converter) 1440 a) to receive control signals, b) to communicate the control signals to the first MEMS sensor 1410 or the second MEMS micro-dispenser 1430, c) to receive the generated IOP measurements from the first MEMS sensor 1410; d) to receive medication dispensing information from the second MEMS micro-dispenser 1430; and e) to communicate the generated IOP measurements and/or the medication dispensing information. In embodiments, a combined IOP measuring and eye medication dispensing device 1400 may comprise a communications interface 1455 to receive the control signals from one or more processors in an external control module, base unit or console, to communicate the control signals to the A-to-D converter, to receive the medication dispensing information or the generated IOP measurements, and to communicate the medication dispensing information and the generated IOP measurements to the external control module, base unit or console. In embodiments, an eye examination wand or probe 1400 may comprise a motion detector 1435. In embodiments, if an eye examination wand or probe is moved, a motion detector 1435 may communicate with a power source 1445 (e.g., battery) to activate an eye examination wand or probe. Similarly, if no motion is detected for a predetermined period of time, then a motion detector 1435 may communicate with a power source 1445 to turn off an examination wand or probe 1400 or go into a sleep mode. In embodiments, an eye examination wand or probe 1400 may be powered via a power source 1445 (e.g., a rechargeable and/or replaceable battery). In embodiments, an eye examination wand or probe 1400 may be powered via a charging port 1450 which may be connected to an external power source (e.g., a wall outlet or a base unit or console). In embodiments, an eye examination wand or probe 1400 may be powered via one or more connections and/or wires in a wired communication interface 1455.

Figure 15:
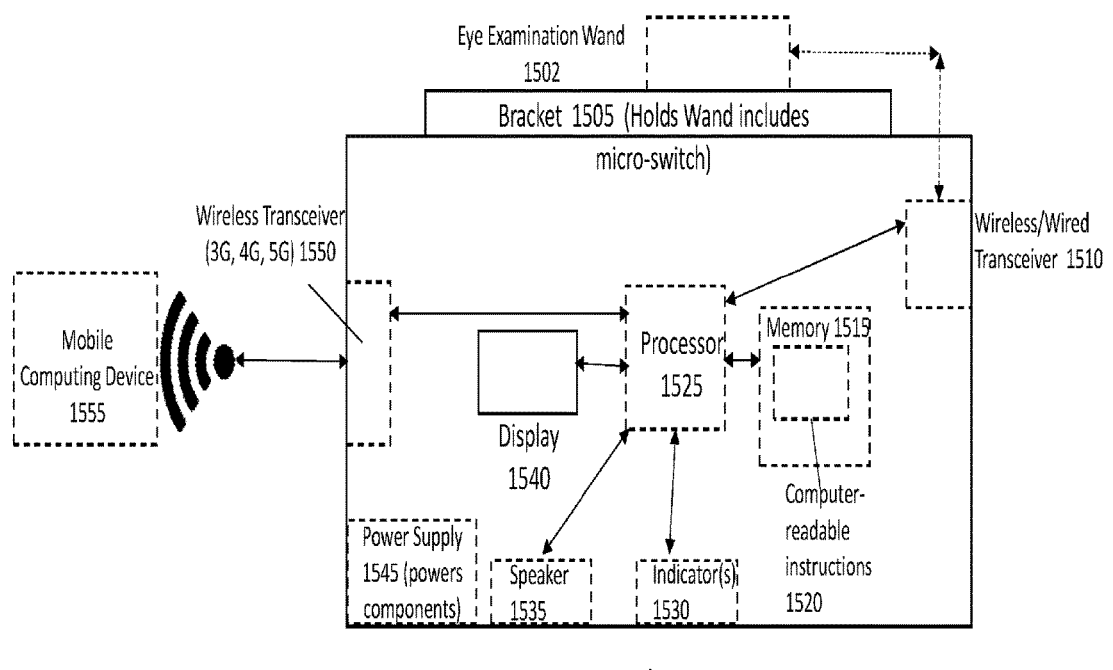
FIG. 15 illustrates a base unit and/or console unit according to embodiments.

FIG. 15 illustrates a base unit and/or console unit according to embodiments. In embodiments, a base unit and/or console unit 1500 includes a bracket 1505 (or other attachment assembly) to which an examination wand or probe 1502 may rest and/or be attached. In embodiments, a bracket 1505 may include a sensor to detect whether an eye examination wand or probe 1502 is present and/or attached to a base unit and/or console unit 1500. In embodiments, a sensor may be a microswitch. In embodiments, if a sensor is active (e.g., the probe is attached), then a base unit and/or console unit 1500 may provide power to an eye examination wand or probe 1502. In embodiments, a base unit and/or console unit 1500 may comprise one or more processors 1525, one or more memory modules or devices 1515, computer-readable instructions 1520 stored in one or more memory modules or devices 1515 and/or a wireless and/or wired communication transceiver 1510 to interface with an eye examination wand or probe 1502. In embodiments, a base unit or console unit may comprise a power supply 1545. In embodiments, a power supply 1545 may be DC powered, AC powered and/or battery powered. In embodiments, a power supply 1545 may be rechargeable and/or removable. In embodiments, a base unit or console unit may comprise one or more indicator and/or alert assemblies. In embodiments, a base unit and/or console unit 1500 may further comprise one or more speakers 1535 (for audible indications of acceptable and error conditions), one or more indicators or lights 1530 (for simple visual indicators of acceptable and error conditions—e.g., green light acceptable condition or red light error condition; green light—power available or device powered up) and/or one or more displays 1540 (for more complex visual indicators of acceptable and error conditions—e.g., messages, numerical displays, alphanumeric displays).

In embodiments, a base unit and/or console unit 1500 may communicate with an eye examination wand or probe 1502 via wireless communication protocols (e.g., PAN transceivers—e.g., Bluetooth wireless communication transceivers; near-field communications (NFC) transceivers; Wi-Fi communication transceivers; or wireless LAN communication transceivers) or via wired communication protocols (e.g., USB transceivers). In embodiments, computer-readable instructions 1520 may be accessed from one or more memory modules 1515 and executed by one or more processors 1525 in a base unit or console 1500 and may generate control signals for operation of an eye examination wand or probe 1502 in either an IOP measurement mode and/or a medication dispensing mode. Thus, the aforementioned executed computer-readable instructions 1520 may generate control signals to measure IOP in a patient's eyes and receive IOP measurements (and associated parameters) from an eye examination wand or probe 1502. In embodiments, received IOP measurements (and associated parameters) may be stored in one or more memory modules 1515 of the base unit or console 1500. In embodiments, the computer-readable instructions 1520 (when executed) may generate control signals to instruct the eye examination wand or probe 1502 to dispense medication into a patient's eye and/or receive medication dispensing parameters. In embodiments, eye medication dispensing parameters may be stored in one or more memory modules 1515 of the base unit or console. In embodiments, a base unit or console unit may comprise a wireless transceiver 1550 to interface with a portable computing device 1555.

In embodiments, a portable computing device 1555 may be a mobile communications device (e.g., a smart phone), a tablet computing device, a desktop computing device, and/or a network device. In embodiments, a wireless transceiver 1550 may operate according to a personal area network (PAN) communications protocol such as Bluetooth or Zigbee; a near field communication (NFC) protocol and/or a cellular communications protocol such as 3G, 4 G (LTE) and/or 5G communication protocols. In embodiments, a base unit or console unit 1500 may retrieve IOP measurements (and associated parameters) and/or medication dispensing parameters (and additional associated parameters) from one or more memory modules 1515 and communicate these measurements and/or parameters utilizing the wireless transceiver 1550 of the base unit or console unit 1500. In embodiments, computer-readable instructions 1520 accessed from the one or more memory modules 1530 and executed by the one or more processors may cause the retrieving and communication of the IOP measurements and medication dispensing parameters and additional information to the mobile computing device 1555. In embodiments, the mobile computing device 1555 may communicate commands, messages and/or instructions to the base unit or console unit 1500 to control operation of the eye examination wand or probe 1502. In embodiments, computer-readable instructions stored in one or more memory modules or devices of a mobile or portable computing device 1555 may be executed by one or more processors (e.g., an eye examination software application) and may interface and/or interact with executed computer-readable instructions on a base unit or console unit 1500 to control operation of an eye examination wand or probe 1502. In other words, part of the software may be executed on a portable computing device 1555 and part of the software may be executed on the base unit or console unit 1500.

Figure 16:
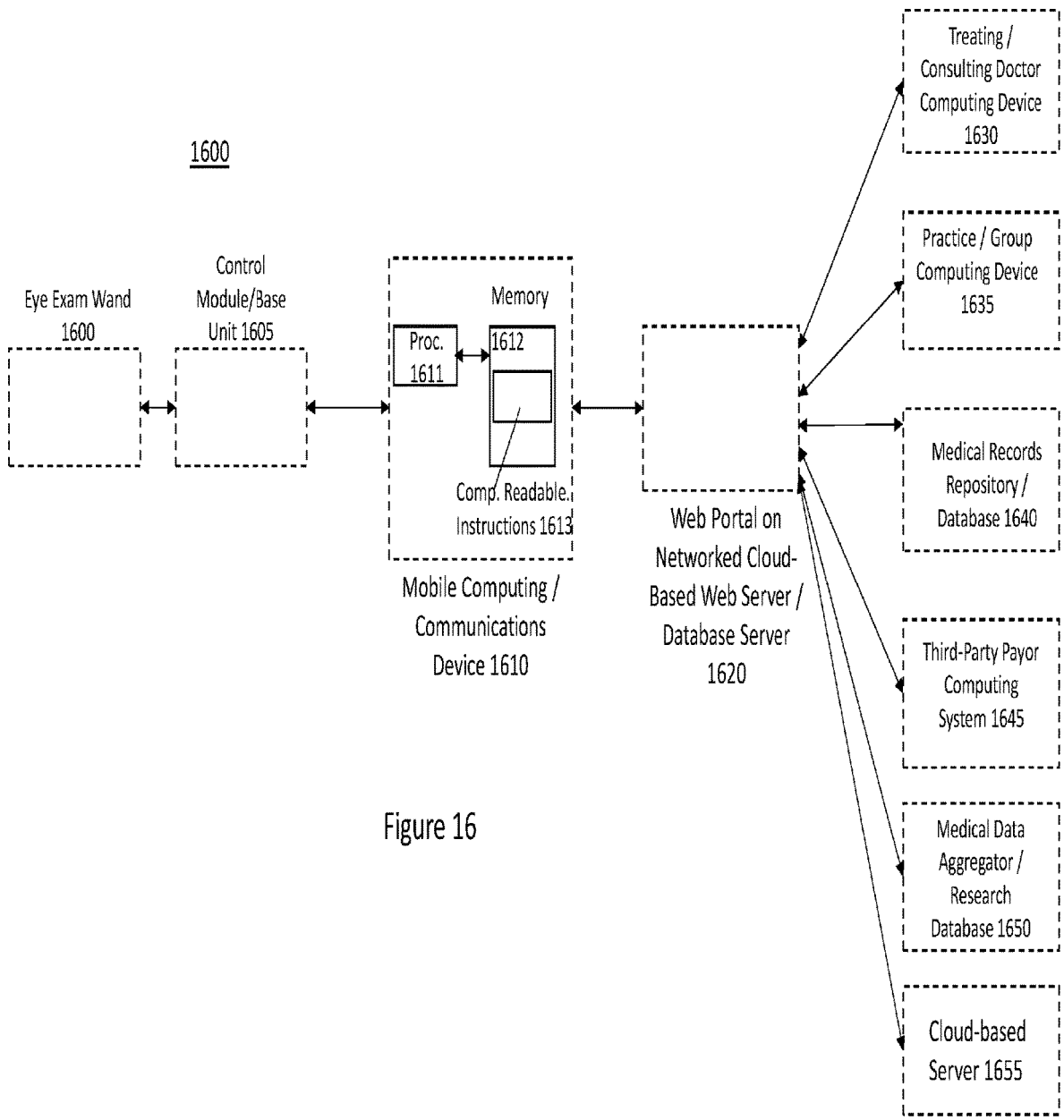
FIG. 16 illustrates an eye examination system for monitoring and/or treating ocular hypertension according to embodiments.

FIG. 16 illustrates an eye examination system for monitoring and/or treating ocular hypertension according to embodiments. In embodiments, an eye examination system 1600 may comprise one or more eye examination wands or probes 1602, one or more base units or control modules 1605, one or more portable computing devices or mobile computing devices 1610 and/or one or more networked cloud-based servers, computing devices, servers, or database servers (which may be accessed via a web portal or other interface or gateway device) 1620. In embodiments, an eye examination system 1600 may further comprise one or more treating or consulting medical provider computing devices or servers 1630, one or more practice or group computing devices or servers 1635, one or more medical record repositories and/or database servers 1640, one or more third-party payor computing devices, servers or systems 1645, one or more medical data aggregator/research database servers 1650, and/or one or more cloud-based servers 1655. In embodiments, an eye examination wand or probe 1602 may comprise a first micro-electro-mechanical system (MEMS) micro-dispenser or sensor assembly to generate IOP measurements, associated timestamps, and associated identifiers and a second MEMS micro-dispenser (or sensor) assembly to dispense eye medication and to generate medication dispensing parameters, associated timestamps and associated identifiers. In embodiments, a base unit or control module 1605 may generate control signals directing operation of the first MEMS sensor assembly and the second MEMS micro-dispenser assembly, may receive generated IOP measurements (as well as timestamps and identifiers) and receive medication dispensing parameters (as well as timestamps and identifiers) and may communicate the generated IOP measurements and medication dispensing parameters to a mobile computing device 1610. In embodiments, the mobile computing device 1610 may receive the generated IOP measurements and medication dispensing parameters. In embodiments, the mobile computing device 1610 may comprise one or more memory devices or modules 1612, one or more processors 1611, and computer-readable instructions 1613 which are stored in the one or more memory modules and/or devices. In embodiments, the computer-readable instructions 1613 may be accessed from the one or more memory devices 1612 and executable by the one or more processors 1611. The accessed computer-readable instructions may be executed by the one or more processors to store the generated IOP measurements and/or medication dispensing measurements and/or parameters as well as to perform all of the functions identified above.

In embodiments, the accessed computer-readable instructions may be executed by the one or more processors to analyze the generated IOP measurements and medication dispensing measurements and to generate medical procedure recommendation messages and/or instructions based at least in part on the received IOP measurements and/or medication dispensing parameters. In embodiments, the accessed computer-readable instructions may be executed by the one or more processors 1611 of the mobile computing device to communicate the IOP measurements, associated parameters (e.g., timestamps), and/or identifiers to one or more remote and/or external computing devices and/or servers via a wireless communication network and a networked web portable or web server 1620. In embodiments, the accessed computer-readable instructions may be executed or executable by the one or more processors 1611 of the mobile computing device to communicate the medication dispensing parameters, additional associated parameters (e.g., timestamps), and/or identifiers to one or more remote and/or external computing devices and/or servers via a wireless communication network and a networked cloud-based web server and/or database server 1620. In embodiments, the received IOP measurements, associated parameters (e.g., timestamps), and/or identifiers and/or the medication dispensing parameters, additional associated parameters (e.g., timestamps), and/or identifiers may be stored in one or more memory modules and/or memory devices of the cloud-based web and/or database server 1620. In embodiments, a networked cloud-based database or web server may be accessed via a web portal by a number of other computing devices and/or servers.

In embodiments, one or more mobile communication devices 1610 may be coupled to a networked cloud-based web server and/or database server 1620 and/or a networked cloud-based web server and/or database server 1620 may be coupled or connected via wireless communications networks and/or wired communications networks to one or more treating/consulting medical provider computing devices 1630, one or more practice or group computing devices 1635, one or more medical record repositories and/or database servers 1640, one or more third-party payor computing devices or systems 1645, one or more medical data aggregator/research database servers 1650, and/or one or more cloud-based servers 1655. In embodiments, the networked cloud-based web server and/or database server 1620 (utilizing a web portal) may be accessed by any of the computing devices and/or servers described immediately above to retrieve stored IOP measurements, associated parameters (e.g., timestamps), and/or identifiers and medication dispensing parameters, additional associated parameters (e.g., timestamps), and/or identifiers. In embodiments, the networked cloud-based web server and/or database server 1620 may communicate with any of these computing devices and/or servers to communicate stored IOP measurements, associated parameters (e.g., timestamps), and/or identifiers and medication dispensing parameters, additional associated parameters (e.g., timestamps), and/or identifiers to these devices. In embodiments, a web portal may reside on a same physical device as a networked cloud-based web server and/or database server 1620 or may reside on a different physical device.

In embodiments, any of the servers or computing devices identified above (e.g., treating or consulting medical provider computing devices or servers 1630, one or more practice or group computing devices or servers 1635, one or more medical record repositories and/or database servers 1640, one or more third-party payor computing devices, servers or systems 1645, one or more medical data aggregator/research database servers 1650, and/or one or more cloud-based servers 1655), may include one or more processors, or microprocessors coupled to one or more non-transitory memory devices and may be adapted to perform the functions described herein. In embodiments, any of the servers and/or computing devices mentioned herein may be any special-purpose machine capable of storing and executing a set of computer-readable instructions (e.g., software) that specify actions to be taken to perform the functions described herein. The mobile computing devices, probes, consoles or base units, the computing devices and servers identified herein are examples of devices including among other components or assemblies, a computer-readable storage medium. The term "computer-readable storage medium" should be taken to include a single medium or multiple media that store one or more sets of instructions. The term "computer-readable storage medium" shall also be taken to include any medium that is capable of storing or encoding a set of instructions for execution by the machine and that causes the machine to perform any one or more of the methodologies of the present disclosure Further, while only a single server or computing device may be illustrated, the term "server" or "computing device(s)" may also be taken to include any collection of machines that individually or jointly execute a set (or multiple sets) of computer-readable instructions to perform any one or more of the methodologies discussed herein. Some of the servers or computing devices identified herein may be located on a same physical computing device. In embodiment, some of the servers or computing devices may be in different physical locations. In embodiments, some servers and/or computing devices may also include at least one database. The database may be a separate component or one that is integrated into one or more servers or computing devices. The database may include any device or combination of devices suitable for storing software, data, information, documentation, instructions and/or parameters for any of the previously mentioned servers or computing devices to assist in performing one or more of the functions described herein.

Figure 17:
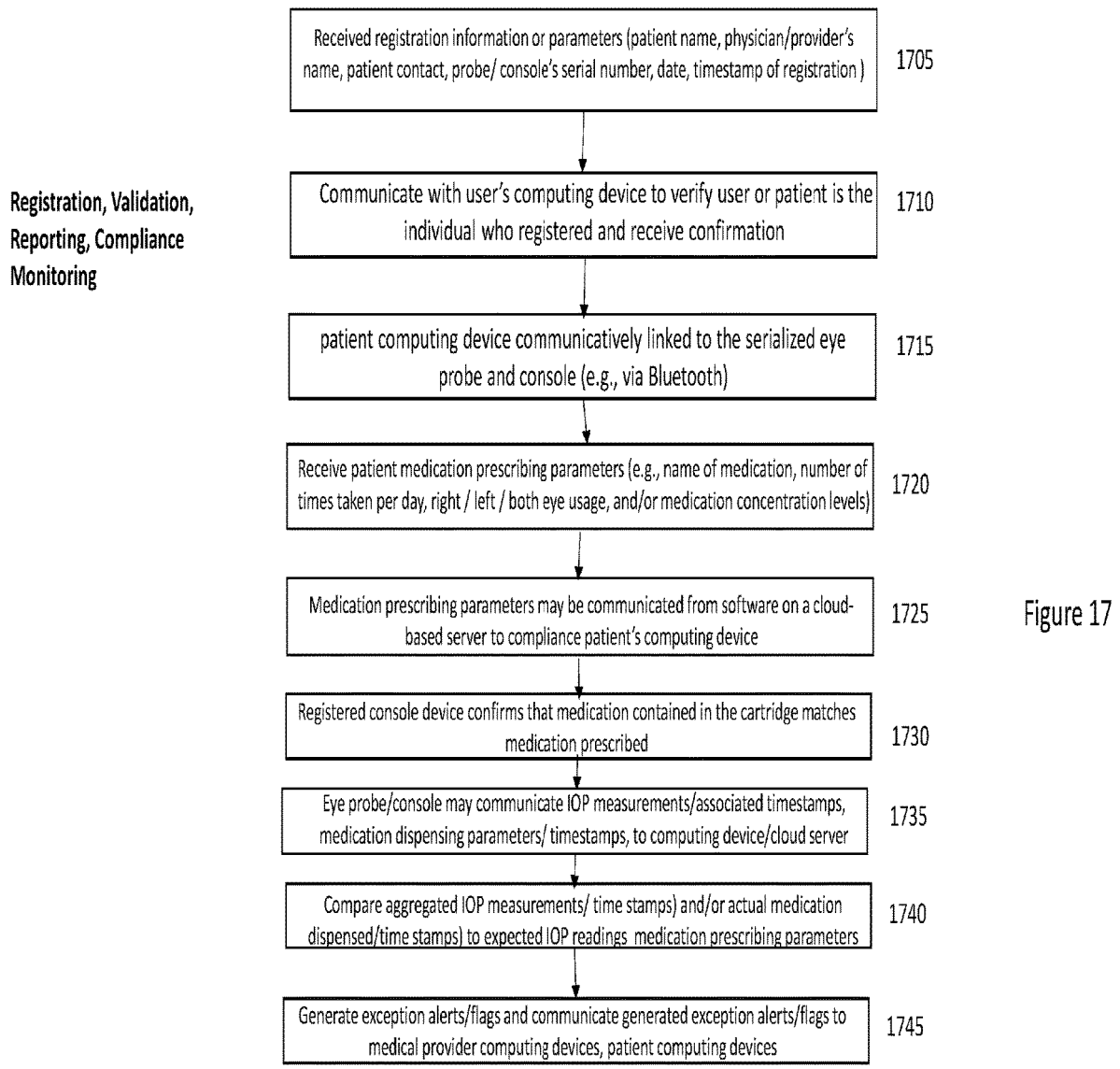
FIG. 17 illustrates a registration, validation, reporting, and compliance monitoring system or process according to embodiments.

FIG. 17 illustrates a registration, validation, reporting, and compliance monitoring system or process according to embodiments. Of course, embodiments are intended to be illustrative examples rather than be limiting with respect to claimed subject matter. Likewise, for ease of explanation, an embodiment may be simplified to illustrate aspects and/or features in a manner that is intended to not obscure claimed subject matter through excessive specificity and/or unnecessary details. Embodiments in accordance with claimed subject matter may include all of, less than, or more than blocks or steps 1700-1745. Also, the order of blocks 1700-1745 is merely as an example order.

In embodiments, a combined eye examination probe is provided to a patient by an eye-care provider. In embodiments, an eye care provider may provide an eye examination probe and/or a console. In embodiments, a medical provider employee (e.g., MD, OD or ophthalmic technician) may enroll a device (e.g., the probe and console) in a compliance monitoring software application. Although the software application is referred to as compliance monitoring, a software application may also perform registration, validation and reporting functionality. In embodiments, a computing device in a medical provider's office may have computer-readable instructions stored in one or more memory modules or device which are retrieved and executed by one or more processors to execute and initiate a compliance monitoring software application. In embodiments, a compliance monitoring software application may receive registration information or parameters 1705 associated with a patient (patient name, physician or provider's name, patient contact parameters, probe's and/or console's serial number, date and/or timestamp when patient registered). In embodiments, a computing device may communicate registration parameters to a cloud-based server hosting compliance monitoring software. In embodiments, each patient may have a separate and unique record due to serialization of eye probe and/or console.

In embodiments, a cloud-based server, hosting compliance monitoring software and/or performing a compliance monitoring process, may communicate 1710 with a user's or patient's computing device to verify user or patient is the individual who registered. In embodiments, a patient may confirm registration either by email, SMS message, iMessage or similar). In embodiments, a patient's computing device may communicate a registration confirmation message to a cloud-based server hosting compliance monitoring software. In embodiments, this confirmation associates a patient account (e.g., and registration parameters) with a unique mobile computing device identifier and/or phone number.

In embodiments, a patient's computing device (e.g., a mobile computing device or a personal computing device) may be communicatively linked 1715 to the serialized eye probe and console. In embodiments, linking may be performed via Bluetooth (if mobile computing device and/or personal computing device is Bluetooth-enabled) or via Wi-Fi (or via NFC or other 802.11 wireless LAN protocols) to a personal computing device and/or mobile computing device. In embodiments, a patient's computing device may communicate such linking information to compliance monitoring software in a cloud-based server.

In embodiments, a patient's medication prescribing parameters may be entered into compliance monitoring software in a medical provider's computing device. In embodiments, a provider's computing device may communicate 1720 the patient's medication prescribing parameters to a cloud-based server computing device as reference information. In embodiments, a patient's computing device may also login to compliance monitoring software on a cloud-based server computing device. In embodiments, this allows a patient and/or a patient advocate to enter medication prescribing parameters and/or modify medication prescribing parameters. In embodiments, medication prescribing parameters may include a name of the medication, a number of times the medication should be taken per day, a right/left/both eye usage, and/or medication concentration levels. In embodiments, dosage and/or regimen may be utilized by the compliance monitoring software on the cloud-based server computing device to know how often to expect data from a linked eye examination probe and/or console device. In the modern era, most patients are on a mono-therapy medication. Mono-therapy is a single drug (such as lanatoprost), which is intended for use once per day. Other medications (such as Timolol) may be prescribed bid (e.g., which is twice per day). Still other medications are available at slightly different concentrations and dosage regimens (e.g., bimatoprost). This informs the cloud-based server computing device how often to expect data from the linked device.

In embodiments, eye medication may be provided in a detachable and replaceable cartridge assembly. Due to the eye's sensitivity as well as the severe consequences if the wrong medication is applied to any part of the eye, it is vital that a medication cartridge be verified before utilized with a patient. In embodiments, some or all of medication prescribing parameters may be communicated 1725 from compliance monitoring software on a cloud-based server computing device to compliance monitoring software on a user or patient's computing device (e.g., mobile computing device and/or personal computing device). In embodiments, compliance monitoring software on a user or patient's computing device may communicate some or all of the medication prescribing parameters to a console unit (if a console and/or probe is registered). In embodiments, after a cartridge assembly is inserted or attached to an eye examination probe, the probe and cartridge assembly may be attached and/or connected to a console device. In embodiments, a registered console device may confirm 1730 that medication contained in the cartridge matches medication prescribed by comparing parameters retrieved from the cartridge with the medication prescribing parameters received from the compliance monitoring software of the cloud-based server computing device. In embodiments, if the cartridge medication matches the medication prescribing parameters, then a console device may display an indicator identifying the cartridge has been validated (e.g., a green light, a sound, a message on a display or control panel). If there is no match, then error indicators may be displayed as well as a console device may generated commands and/or messages to be communicated to compliance monitoring software on a patient's computing device and/or compliance monitoring software resident on a cloud-based server computing device.

In embodiments, if a console itself does not store and/or have medication prescribing parameters for a patient, a console may communicate with a patient's computing device and/or compliance monitoring software on the cloud-based server computing device to verify the cartridge has the correct prescribed medicine. Once this has been completed and the medication has been validated, a patient and/or patient advocate may utilize the dual-purpose probe to measure IOP and/or apply medication to a patient's eye.

In embodiments, an eye probe may generate IOP measurements and timestamps and may communicate the generated IOP measurements and timestamps. In embodiments, an eye probe may generate medication dispensing parameters (e.g., which may include timestamps) and the console device may communicate the medication dispensing parameters to confirm that IOP-lowering medication has been dispensed. In embodiments, an eye probe and/or console may communicate 1735 IOP measurements and associated timestamps, and/or medication dispensing parameters and/or timestamps, to a patient's computing device (e.g., compliance monitoring software) and/or to a cloud-based server computing device (e.g., compliance monitoring software on a cloud-based server device). In embodiments, compliance monitoring software on a cloud-based server computing device may, on a periodic basis, (e.g., monthly (or weekly or quarterly)) generate aggregate reporting summaries for individual patients and/or for more than one patient of an eye care provider. In embodiments, compliance monitoring software on a cloud-based server computing device may communicate aggregate reports to a patient's computing device for review by a patient. In embodiments, compliance monitoring software on a cloud-based server computing device may communicated aggregate reports for one or more patients to a medical provider's computing device for review by medical provider's practitioners.

In embodiments, compliance monitoring software on a cloud-based server computing device may compare 1740 aggregated IOP measurements (and associated time stamps) and/or actual medication dispensed (and associated time stamps) to expected IOP readings (and timing) medication prescribing parameters (and timing) that had been entered previously. In embodiments, compliance monitoring software on a cloud-based server may generate 1745 exception alerts and/or flags and may communicate generated exception alerts and/or flags to medical provider computing devices, patient computing devices, third-party payor computing devices, researcher computing devices and/or data aggregator computing devices. In embodiments, compliance monitoring software on a cloud-based server computing device may generate exception reports (and/or aggregated exception reports) and may communicate generated exception reports (and/or aggregated exception reports) to medical provider computing devices, patient computing devices, third-party payor computing devices, researcher computing devices and/or data aggregator computing devices.

In embodiments, a computer-implemented method may monitor glaucoma parameters and medication delivery compliance and may include the steps of receiving registration information or parameters, communicate with an user's computing device to verify user or patient is the individual who registered; receive confirmation that the user or patient is registered; and communicatively link, via a Bluetooth wireless communication transceiver, a patient computing device to a serialized eye probe and console. In embodiments, the computer-implemented method may also receive patient medication prescribing parameters for the patient; communicate medication prescribing parameters from software on a cloud-based server computing device to a user or patient's computing device; confirm, by the console device that medication contained in a cartridge matches a medication prescribed for the patient; and communicate, by the console device, IOP measurements and associated timestamps, medication dispensing parameters and timestamps, to the patient computing device and/or the cloud-based server computing device. In embodiments, the computer-implemented method may also compare, at the cloud-based server computing device, aggregated IOP measurements and associated time stamps and/or actual medication dispensed and associated time stamps) to expected IOP readings and medication prescribing parameters for the patient; and generate, at the cloud-based server computing device, exception alerts or flags and communicating the generated exception alerts or flags to a medical provider computing device or the patient computing device. In embodiments, the registration information or parameters may comprise a patient name, a physician or provider's name, a patient contact, a probe or console serial number, a date or a timestamp of registration. In embodiments, the patient medication prescribing parameters may comprise a medication name, a number of times medication is to be taken per day, whether the medication should be used in the right eye, left eye or both eyes, and/or medication concentration levels.

In embodiments, a mobile communication and/or computing device (e.g., smartphone) may be replaced by a tablet or other low cost or portable computing device; a full feature desktop and/or laptop personal computer, a single-board computer in an electronic device, a wearable computing device, and/or an integrated computer on a printed circuit board in an electronic device or computing device.

In embodiments, images, measurements, information and/or other data may be communicated in compressed, encrypted and/or encoded form between portable computing devices, servers, databases, consoles, base units and/or eye examination wands. Further, in embodiments, computing devices (e.g., mobile, portable, servers, etc.) may include components, circuits and/or assemblies to perform compression/decompression; encryption/decryption; and/or encoding/decoding.

In embodiments, communications over a communication channel utilized by a mobile communication and/or computing devices (e.g., smartphone) (e.g., Bluetooth, USB, Zigbee, 802.11, 3 G, 4G, 5 G), may include a serial number that corresponds to hardware or devices and that may be communicated to other mobile communication and/or computing device (e.g., smartphone) and/or computing devices, servers, databases, etc. to prevent unauthorized use of a system.

This system and method may utilize a "smart" device that communicates with the Internet over Wi-Fi (802.11 G and similar) networks, NFC networks, and personal area networks rather than cellular (3G) networks. For example, an Apple iPod Touch® contains a hi-resolution camera and processing chipsets comparable to an Apple iPhone®, but does not contain 3 G chipsets for cellular communications.

For the purposes of this disclosure a computer-readable medium stores computer-readable instructions, the computer-readable instructions may include computer program code that is executable by one or more processors. In embodiments, for example, and not being read as limiting, a computer readable medium may comprise computer-readable storage media, for tangible or fixed storage of data, or communication media for transient interpretation of code-containing signals. Computer-readable storage media, as used herein, may refer to physical and/or tangible storage (as opposed to signals) and may include, without limitation, volatile and non-volatile, removable and non-removable media, implemented and embodied, in any method or technology for the tangible storage of information, such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer and/or processor.

For the purposes of this disclosure, a system or module may be software, hardware, or firmware (or combinations thereof), process or functionality, or component thereof, that performs or facilitates the processes, features, and/or functions described herein (with or without human interaction or augmentation). In embodiments, a module can include submodules, subroutines, components, subcomponents. In embodiments, software components and/or subcomponents of a module may be stored on a computer readable medium. In embodiments, systems and/or modules may be integral to and/or installed one or more computing devices (e.g., application servers, database servers, personal computing devices, portable computing devices, laptop computing devices, wearable computing devices, mobile application servers, and/or cloud-based servers) may be loaded and executed by one or more processors on one or more computing device. In embodiments, one or more software systems and/or modules may be grouped into an engine and/or an application.

Those skilled in the art may recognize that the methods, apparatus and systems of the present disclosure may be implemented in many manners and, as such are not to be limited by the foregoing exemplary embodiments and/or examples. In other words, functional elements being performed by single or multiple components, in various combinations of hardware and software or firmware, and individual functions, may be distributed among software applications at either the client or server, or multiple computing devices, or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components and/or assemblies, in manners now known or to become known. Thus, myriad software/hardware/firmware combinations may be possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

In embodiments, communications between a mobile computing device or computing device and/or a network device and a wireless network may be in accordance with known and/or to be developed communication network protocols including, for example, global system for mobile communications (GSM), enhanced data rate for GSM evolution (EDGE), 802.11b/g/n, and/or worldwide interoperability for microwave access (WiMAX). In embodiments, a mobile computing device or a computing device and/or a networking device may also have a subscriber identity module (SIM) card, which, for example, may comprise a detachable smart card that is able to store subscription content of a user, and/or is also able to store a contact list of the user. In embodiments, a user may own a mobile computing device or a computing device and/or networking device or may otherwise be a user, such as a primary user, for example. In embodiments, a mobile computing device or computing device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a communication network may be embodied as a wired network, wireless network, or any combinations thereof.

Algorithmic descriptions and/or symbolic representations are examples of techniques used by those of ordinary skill in the signal processing and/or related arts to convey the substance of their work to others skilled in the art. An algorithm here, and generally, is considered to be a self-consistent sequence of operations and/or similar signal processing leading to a desired result. In this context, operations and/or processing involve physical manipulation of physical quantities. Typically, although not necessarily, such quantities may take the form of electrical and/or magnetic signals and/or states capable of being stored, transferred, combined, compared, processed or otherwise manipulated as electronic signals and/or states representing various forms of content, such as signal measurements, text, images, video, audio, etc. It has proven convenient at times, principally for reasons of common usage, to refer to such physical signals and/or physical states as bits, values, elements, symbols, characters, terms, numbers, numerals, measurements, content and/or the like. It should be understood, however, that all of these and/or similar terms are to be associated with appropriate physical quantities and are merely convenient labels. Unless specifically stated otherwise, as apparent from the preceding discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing and/or network device. In the context of this specification, therefore, a special purpose computer and/or a similar special purpose computing and/or network device is capable of processing, manipulating and/or transforming signals and/or states, typically represented as physical electronic and/or magnetic quantities within memories, registers, and/or other storage devices, transmission devices, and/or display devices of the special purpose computer and/or similar special purpose computing and/or network device. In the context of this particular patent application, as mentioned, the term "specific apparatus" may include a general-purpose computing and/or network device, such as a general-purpose computer, once it is programmed to perform particular functions pursuant to instructions from program software.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all implementations falling within the scope of the appended claims, and equivalents thereof.

The invention claimed is:

1. An eye examination system for treating glaucoma and ocular hypertension, comprising:
an eye examination wand, the eye examination wand comprising:
a first micro-electro-mechanical system (MEMS) sensor assembly configured to generate IOP measurements and associated timestamps, and
a second MEMS micro-dispenser assembly configured to a) dispense specific microscopic volumes of solution containing eye medication; and b) generate medication dispensing parameters and associated timestamps; and
a base control device configured to generate control signals, the control signals to direct operation of the first MEMS sensor assembly and the second MEMS micro-dispenser assembly, the base control device further configured to receive the generated IOP measurements and receive the medication dispensing parameters, and configured to communicate the generated IOP measurements and the medication dispensing parameters to a mobile computing device,
wherein the first MEMS sensor assembly and the second MEMS micro-dispenser assembly are positioned at a distal end of a body of the eye examination wand.

2. The eye examination system of claim 1, the mobile computing device comprising one or more memory devices, one or more processors and computer-readable instructions executable by the one or more processors to:
receive the generated IOP measurements and the medication dispensing parameters; and
store, in the one or more memory devices, the received IOP measurements and the medication dispensing parameters.

3. The eye examination system of claim 1, the base control device comprising a microswitch, the microswitch configured to detect movement of the eye examination wand and to wake up components of the base control device or the eye examination wand.

4. The eye examination system of claim 3, the base control device configured to execute a self-check to confirm the eye examination system is ready and to generate commands to activate the first MEMS sensor assembly.

5. The eye examination system of claim 1, the base control device comprising one or more speakers, the one or more speakers configured to generate audible indications of acceptable or error conditions.

6. The eye examination system of claim 1, the base control device comprising one or more indicators or lights, the one or more indicators or lights configured to generate visual indications of acceptable or error conditions.

7. The eye examination system of claim 1, the base control device comprising one or more displays, the one or more displays configured to generate messages, numerical displays, or alphanumeric displays.

8. The eye examination system of claim 1, the computer-readable instructions further executable by the one or more processors to:
analyze the received IOP measurements and the received medication dispensing parameters; and
generate medical procedure recommendation messages, based at least in part, on the received IOP measurements and the received medication dispensing parameters.

9. The eye examination system of claim 1, further comprising a remote computing device, the remote computing device being at a different physical location from the mobile computing device, the computer-readable instructions of the mobile computing device executable by the one or more processors of the mobile computing device to communicate the received IOP measurements and the received medication dispensing parameters to the remote computing device.

10. The eye examination system of claim 9, the remote computing device comprising a cloud-based server computing device; an email server computing device; a text server computing device; a medical records repository computing device, a medical billing computing device, a third-party payor's computing device, a physician's computing device, or another mobile computing device.

11. The eye examination system of claim 1, the base control device configured to further receive timestamps and identifiers associated with the received IOP measurements and timestamps and identifiers associated with the received medication dispensing parameters and configured to communicate the timestamps and identifiers associated with the received IOP measurements and the timestamps and identifiers associated with the received medication dispensing parameters to the mobile computing device.

12. An eye examination wand including an eye medication dispensing device configured to deliver medication to a living organism's eye, comprising:
a reservoir configured to hold eye medication;
one or more nozzles configured to dispense the eye medication into the living organism's eye;
a micro-electro-mechanical-system (MEMS) micro-dispenser configured to interact with the reservoir to control dispensing of the eye medication;
an analog-to-digital (A-to-D) converter configured: to receive digital control signals, convert the digital control signals to analog control signals, to communicate the analog control signals to a MEMS sensor, to receive analog medication dispensing parameters from the MEMS micro-dispenser; convert the analog medication dispensing parameter to digital medication dispensing parameters, and communicate the digital medication dispensing parameters; and
a communications interface configured: to receive digital control signals from one or more processors in an external control module, to communicate the digital control signals to the A-to-D converter, to receive the digital medication dispensing parameters, and to communicate the digital medication dispensing parameters to the external control module,
wherein the MEMS sensor and the MEMS micro-dispenser are positioned at a distal end of a body of the eye examination wand.

13. The eye examination wand of claim 12, wherein the communications interface is a wireless communication interface.

14. The eye examination wand of claim 13, wherein the wireless communications interface is a Bluetooth wireless communication transceiver.

15. The eye examination wand of claim 13, wherein the wireless communications interface is a Wi-Fi communication transceiver, a near-field communications ("NFC") transceiver, a personal area network (PAN) transceiver, or a wireless local area network (LAN) transceiver.

16. A combined intraocular pressure (IOP) measuring and eye medication dispensing device, comprising:
- a first micro-electro-mechanical-system (MEMS) sensor configured to generate IOP measurements of a living organism's eye by pressing the first MEMS sensor against a surface of the living organism's eye;
- a medication dispensing device configured to dispense medication into the living organism's eye;
- a second MEMS micro-dispenser configured to interface with the medication dispensing device and configured to control the dispensing of the medication into the living organism's eye;
- an eye examination wand apparatus configured: to receive control signals, to communicate the control signals to the first MEMS sensor or the second MEMS micro-dispenser, to receive the generated IOP measurements from the first MEMS sensor; to receive medication dispensing parameters from the second MEMS micro-dispenser or medication dispensing device and to communicate the generated IOP measurements or the medication dispensing parameters; and
- a communications interface configured: to receive the control signals from one or more processors in an external control module, to communicate the control signals to the eye examination wand apparatus, to receive the medication dispensing parameters or the generated IOP measurements, and to communicate the medication dispensing parameters or the generated IOP measurements to the external control module,
- wherein the first MEMS sensor and the second MEMS micro-dispenser are positioned at a distal end of the eye examination wand apparatus.

17. The combined IOP measuring and eye medication dispensing device of claim 16 and further comprising a mobile computing device, the mobile computing device comprising one or more memory devices, one or more processors and computer-readable instructions executable by the one or more processors to:
- receive the generated IOP measurements and the medication dispensing parameters; and
- store, in the one or more memory devices, the received generated IOP measurements and the received medication dispensing parameters.

18. The combined IOP measuring and eye medication dispensing device of claim 17, further comprising a remote computing device, the remote computing device being a different computing device than the mobile computing device, the computer-readable instructions of the mobile computing device executable by the one or more processors of the mobile computing device to communicate the received generated IOP measurements and the received medication dispensing parameters to the remote computing device.

19. The combined IOP measuring and eye medication dispensing device of claim 18, the remote computing device comprising a cloud-based server computing device; an email server computing device; a text server computing device; a medical records repository computing device, a medical billing computing device, a third-party payor's computing device, a physician's computing device or another mobile computing device.

20. The combined IOP measuring and eye medication dispensing device of claim 16, the medication dispensing device comprising a medication reservoir configured to hold the medication and one or more nozzles or dispensers configured to dispense the medication, the second MEMS micro-dispenser to control the dispensing of the medication from the medication reservoir through the one or more nozzles or dispensers into the living organism's eye.

* * * * *